United States Patent [19]

Ayres

[11] Patent Number: 4,581,359

[45] Date of Patent: Apr. 8, 1986

[54] PHARMACOLOGICAL TREATMENTS WITH N-7-SUBSTITUTED DERIVATIVES OF THEOPHYLLINE

[75] Inventor: James W. Ayres, Corvallis, Oreg.

[73] Assignee: The State of Oregon Acting by and through the Oregon State Board of Higher Education on behalf of Oregon State University, Eugene, Oreg.

[21] Appl. No.: 602,665

[22] Filed: Apr. 23, 1984

[51] Int. Cl.⁴ ............................................. A61K 31/52
[52] U.S. Cl. .................................... 514/264; 514/263; 514/826
[58] Field of Search ................ 424/253; 514/263, 264, 514/826

[56] References Cited

U.S. PATENT DOCUMENTS 4,031,218 6/1977 El-Antably ......................... 424/253

OTHER PUBLICATIONS

"The Merck Index", 9th Ed., 1976, paragraphs 3455, 3828, 7691 and 9004.
*Martindale, The Extra Pharmocopia*, 28th Ed., pp. 347, 348, and 1262 (1982).
*Rote Liste*, 1977/78, paragraphs 27 015 B and 54 120 B.
Boardman, "Interactions between Theophylline and Theophylline Derivates in Producing Relaxation of Guinea-Pig Isolated Tracheal Chains", *Proceedings of the B.P.S.*, 9th-11th, pp. 120P-121P (Apr. 1980).
Bracher et al., "Pharmakokinetik und klinische Wirksamkeit rektal verabreichter Theophylline", *Respiration*, 43:458-466 (1982).
Bussey, "Theophylline Toxicity After Dyphylline Therapy", *Am. Rev. Resp. Dis.*, 124:504 (1981).
"I.V. Dosage Guidelines for Theophylline Products," *FDA Drug Bulletin*, 10:4-6 (1980).
Furukawa et al., "Dyphylline versus Theophylline: A Double Blind Comparative Evaluation", *J. Clin. Pharmacol.*, 23:414-418 (1983).
Gisclon et al., "Pharmacokinetics of Orally Administered Dyphylline", *Am. J. Hosp. Pharmacy*, 36:1179-1184 (1979).
Graffner et al., "Pharmacokinetic Studies on Proxyphylline Administered Intravenously and Orally to Man", *Acta Pharmaceutica Suecia*, 10:425-434 (1973).
Hendeles et al., "Dyphylline: The 'Untheophylline' Xanthine Bronchodilator", Editorial, *Drug Intelligence & Clin. Pharm.*, 11:424 (1977).
Hendeles et al., "Poisoning Patients with Intravenous Theophylline," *Am. J. Hosp. Pharm.*, 37:49-50 (1980).
Isaksson et al., "Blood Plasma Level of Different Theophylline Derivatives Following Parenteral, Oral and Rectal Administration", *Acta Medica Scandinavica*, 171:33-38 (1962).

(List continued on next page.)

*Primary Examiner*—Leonard Schenkman
*Attorney, Agent, or Firm*—Klarquist, Sparkman, Campbell, Leigh & Whinston

[57] ABSTRACT

Methods for the management of bronchopulmonary insufficiency and other conditions are disclosed. The methods involve administration of an N-7-substituted derivative of theophylline selected from the group consisting of dyphylline, etophylline, proxyphylline and mixtures thereof. The derivative can be administered intravenously, intramuscularly, or in the lungs, concurrently with some form of theophylline or administered alone to a patient whose body has a known or an unknown theophylline content. Theophylline and the derivative can be administered in the same dosage form or in separate dosage forms. They can have the same route of administration or different routes of administration; for example, theophylline can be given orally, while the derivative is given as a zero-order intravenous infusion. A high total plasma concentration of methyl xanthine is achieved safely by using a combination of theophylline and one or more of the derivatives. Rapid injection of a loading dose of the derivative is also disclosed.

12 Claims, 11 Drawing Figures

OTHER PUBLICATIONS

Joos et al., "Gekreuzter Doppeltbindversuch mit Neophyllin oral (Proxyphyllin und Diprophyllin) bei Asthma bronchiale", *Schweiz. Med. Wschr.*, 109:726-731 (1979).

Lawyer et al., "Utilization of Intravenous Dihydroxypropyl Theophylline (Dyphylline) in an Aminophylline-Sensitive Patient, and its Pharmacokinetic Comparison with Theophylline", *J. Allergy & Clin. Immunol.*, 65:353-357 (1980).

McColl et al., "A Comparison of the Relative Toxic, Emetic and Convulsive Actions of a Series of Methylated Xanthine Derivatives", *J. Pharmacol. & Experimental Therapeutics*, pp. 343-350 (1955).

Merkus et al., "Theophylline and Hydroxyethyltheophylline are Different Drugs", *Int. J. Clin. Pharmacol., Therapy & i Toxicol.*, 18:97 (1980).

Palmer et al., "Comparison of Drugs for Asthma", *Brit. Med. J.*, p. 727 (Mar. 1971).

*Physicians Desk Reference*, 21st Edition, Medical Economics, Inc., Oradell, N.J., pp. 1014-1015 (1967).

*Physicians Desk Reference*, 23rd Edition, Medical Economics, Inc., Oradell, N.J., pp. 856-857 (1969).

*Physicians Desk Reference*, 35th Edition, Medical Economics Company, Oradell, N.J., pp. 1025-1027, 1584, 1861-1863 (1981).

Poyner, "Dyphylline Pharmacokinetics Following Two Consecutive Intravenous Infusions in Beagle Dogs," Doctor of Philosophy Dissertation, the University of Texas at Austin, Austin, Tex., 1980.

*Remington's*, 16th Edition, The Philadelphia College of Pharmacy, 43:810-811.

Selvig, "Metabolism of Proxyphylline in Man: Urinary Excretion of Proxyphylline and Its Metabolites", *Drug Metabolism & Disposition*, 10:291-292 (1982).

Selvig et al., "Metabolism of Proxyphylline in Man, Isolation and Identification of Metabolites in Urine," *Drug Metabolism & Disposition*, 8:456-462 (1980).

Sharma et al., "Comparative Bioavailability of Sustained-Release and Conventional Tablets of Hydroxyethyltheophylline in Man", *Int. J. Clin. Pharmacol. & Biopharm.*, 17:394-396 (1979).

Tivenius, "Comparison of Drugs for Asthma", *Brit. Med. J.*, p. 773 (Jun. 1971).

Ufkes et al., "Efficacy of Theophylline and its N-7--Substituted Derivatives in Experimentally Induced Bronchial Asthma in the Guinea-Pig", *Arch. Int. Pharmacodyn.*, 253:301-314 (1981).

*Unlisted Drugs*, 28:178 (Oct. 1976).

*Unlisted Drugs*, 31:58 (Apr. 1979).

Werdermann et al., "Zur bronchodilatatorischen Wirkung von Methylxanthinderivaten", *Deutsche Med. Wschr.*, 104:1307-1311 (1979).

Zuidema et al., "Is Acephylline a Theophylline Bronchodilator?", *The Lancet*, pp. 1318-1319 (Jun. 17, 1978).

Zuidema et al., "Chemical and Biopharmaceutical Aspects of Theophylline and its Derivatives", *Cur. Med. Res. & Opinion, 6:14-25 (1979)*.

Zuidema et al., "N-Substituted Theophylline Derivatives", *Am. J. Hosp. Pharm.*, 37:169-170 (1980).

Zuidema et al., "Pharmacokinetics and Pharmacodynamics of Diprophylline", *Pharmaceutisch Weekblad*, 3:1320-1325 (1981).

Zuidema et al., "Pharmacokinetics of Etophylline after Intravenous and Oral Administration to Humans", *Int. J. Clin. Pharmacol., Therapy & Toxicol.*, 19:310-313 (1981).

PHARMACOLOGICAL TREATMENTS WITH N-7-SUBSTITUTED DERIVATIVES OF THEOPHYLLINE

SUMMARY OF THE INVENTION

The present invention relates to the management of bronchopulmonary insufficiency by administration of methyl xanthine preparations. In particular, the present invention relates to particular uses of certain N-7-substituted derivatives of theophylline.

Theophylline and its salts, such as aminophylline, are known to be useful in treatment of various types of bronchopulmonary insufficiency. The efficacy and toxicity of these substances has been widely studied. For instance, only a few references of hundreds available would be: Goodman et al., *The Pharmacological Basis of Therapeutics*, 6th Edition, edited by Alfred Goodman Gilman, Louis S. Goodman and Alfred Gilman, Macmillan Publishing Co., Inc., New York, N.Y., pp 592–607, 1732 (1980); Krupp and Chatton, *Current Medical Diagnosis and Treatment*, Lange Medical Publications, Los Altos, Calif., pp 111–114, 978 (1982); *Harrisons Principles of Internal Medicine*, 8th Ed., edited by Thorn et al., McGraw-Hill Book Co., New York, N.Y., pp 345, 1353–1361 (1977); Hendeles and Weinberger, "Poisoning Patients with Intravenous Theophylline," *American Journal of Hospital Pharmacy*, Vol. 37, pp 49–50 (1980); Svedmyr, *Scand. J. of Resp. Dis.*, 1977 Supplement No. 101, pp 126–137 (1977); *Physicians Desk Reference*, 35th Edition, Medical Economics Company, Oradell, N.J. (1981); and "I.V. Dosage Guidelines for Theophylline Products," *FDA Drug Bulletin*, Vol. 10, pp 4–6 (1980). Sustained action dosage forms of theophylline are well known and marketed by many major drug companies.

Thus, it is well known that theophylline is both clinically effective for the treatment of bronchopulmonary insufficiency and toxic when administered orally or intravenously, and that the dose must be very carefully controlled and administered gradually, over a period of time to properly use this drug. If an excessive dose is given or if a total effective dose of the theophylline is administered too rapidly, i.e., in less than about twenty minutes, the subject will experience a blood pressure drop and may develop convulsions which in some instances lead to death.

N-substituted derivatives of theophylline, such as dyphylline, etophylline, and acephylline also have been studied. For example, dyphylline is known to have a high water solubility, lower toxicity than theophylline, and lower effectiveness than theophylline for the treatment of bronchopulmonary insufficiency. Some of the references available include: *Physicians Desk Reference*, 35th Edition; Svedmyr; Goodman et al., p. 601; Lawyer et al., "Utilization of Intravenous Dihydroxypropyl Theophylline (dyphylline) in an Aminophylline-Sensitive Patient, and its Pharmacokinetic Comparison with Theophylline", *J. Allergy and Clin. Immunol.*, pp 353–357 (1980); *Physicians Desk Reference*, 21st Edition, Medical Economics, Inc., Oradell, N.J. (1967); *Physicians Desk Reference*, 23rd Edition, Medical Economics, Inc., Oradell, N.J. (1969); Gisclon et al., "Pharmacokinetics of Orally Administered Dyphylline", *Am. J. Hosp. Pharmacy*, pp 1179–1184 (1979); Zuidema et al., "Pharmacokinetics and Pharmacodynamics of Diprophylline", *Pharmaceutisch Weekblad*, pp 1320–1325 (1981); *Current Medical Research and Opinion*, Vol. 6, Supplement 6, pp. 14–25 (1979); McColl et al., "A comparison of the Relative Toxic, Emetic and Convulsive Actions of a Series of Methylated Xanthine Derivatives", *Journal of Pharmacology and Experimental Therapeutics*, pp 343–350 (1955); Simons et al., "Efficacy of Dyphylline (dihydroxypropyltheophylline) in Exercise-Induced Bronchospasm", *Pediatrics*, Vol. 56 (Supplement), pp 916–918 (1975); Hendeles et al., "Dyphylline: The 'Untheophylline' Xanthine Bronchodilator", Editorial, *Drug Intelligence and Clinical Pharmacy*, Vol. 11, p. 424 (1977); Hendeles et al., "Poor Absorption of an Untheophylline Xanthine Bronchodilator", *Am. J. Hosp. Pharmacy*, Vol. 37. pp 169 (1980); Zuidema et al., "N-substituted Theophylline Derivatives", *Am. J. Hosp. Pharmacy*, Vol. 37, pp 169–170 (1980); Bussey, "Theophylline Toxicity After Dyphylline Therapy", *Am. Rev. Respiratory Disease*, p 504 (1981); Lewis, "Deletion of Dyphylline from the Formulary", *Hosp. Pharmacy*, Vol. 16, pp 429–430 (1981); Isaksson et al., "Blood Plasma Level of Different Theophylline Derivatives Following Parenteral, Oral and Rectal Administration", *Acta Medica Scandinavica*, Vol. 171, pp 33–38 (1962); Maney et al., "Dihydroxypropyl Theophylline: Its Preparation and Pharmacological and Clinical Study", *J. Am. Pharmaceutical Ass.*, Scientific Edition, Vol. 35, pp 266–272 (1946); Simons et al., "The Pharmacokinetics of dihydroxypropyltheophylline: A basis for Rational Therapy", *Allergy and Clin. Immunol.*, Vol. 56, pp 347–355 (1975); Ouellette et al., "Efficacy and Tolerability of Dyphylline (Luffyllin ®) in Bronchial Asthma: A Retrospective Study", *Current Therapeutic Research*, Vol. 27, pp 844–851 (1980). Dyphylline also has been administered as a sustained action product by Simons et al., "Bioavailability of a Sustained Release Dyphylline Fermentation", *J. Clin. Pharmacol.* 17:237–242 (1977).

For dyphylline, there is a great diversity of opinion regarding its effectiveness with a clear majority of researchers proposing that it should not be used and a very few indicating that it is a useful drug following oral administration. It is generally agreed that dyphylline is less effective and toxic than theophylline, and that it can cause gastrointestinal irritation, central nervous system stimulation, clonic and tonic generalized convulsions and cardiovascular palpitation or tachycardia.

The effective dose-response relationship for dyphylline is not well defined. The literature in this area has been well reviewed by Poyner (Wesley Jim Poynor, "Dyphylline Pharmacokinetics Following Two Consecutive Intravenous Infusions in Beagle Dogs," Doctor of Philosophy Dissertation, the University of Texas at Austin, Austin, Tex., 1980). In one poorly controlled study (no placebo, no cross-over, no double-blinding) with eighty-six patients, dyphylline was found to be effective at a dose of 200 mg four times daily and plasma levels of 7.0 to 10.0 mcg/ml: Levine, "An effective Oral Medication for Long Term Bronchodilation", *Ann. Allergy*, Vol. 23, pp 403–413 (1965). Simons et al., reported, in "The Pharmacokinetics of dihydroxypropyltheophylline: A basis for Rational Therapy", *Allergy and Clin. Immunol.*, Vol. 56, pp 347–355 (1975), that 12.3 mcg/ml of dyphylline in plasma was effective but 7.19 mcg/ml was not effective. Hudson et al., "Oral Aminophylline and Dihydroxypropyul Theophylline in Reversible Obstructive Airway Disease: A single-Dose, Double Blind, Cross-over Comparison", *Curr. Ther.*

Res. Vol 15, pp. 367–372, (1973) reports that plasma concentrations of 16.3 mcg/ml of dyphylline were minimally effective and 9.3 mcg/ml were not effective. It was estimated that a dose of at least 2000 mg would be required to equal the therapeutic response of a dose of 500 mg of aminophylline which would presumably yield a plasma dyphylline concentration of 30 to 35 mcg/ml (Poyner, pp. 1, 18). Furukawa et al., in "Dyphylline versus Theophylline: A Double Blind Comparative Evaluation", J. Clin. Pharmacol., 23:414–418 (1983), indicate that theophylline is more effective and toxic than dyphylline and that dyphylline causes dizziness, stomach problems, headache, and especially tremors. Plasma concentrations of 15 mcg/ml had some limited beneficial effect on bronchoconstriction.

Lawyer et al., concluded that dyphylline doses of about 5 to 6 times theophylline doses are required to produce equivalent bronchodilator response. Svedmyr states that using in vitro studies, dyphylline (glyphylline) is ten times weaker than theophylline. Poyner, at pp 20–21, states that dyphylline is a suitable candidate for intravenous use in patients with acute attacks of asthma and hepatic dysfunction. Zuidema et al., in "Chemical and Biopharmaceutical Aspects of Theophylline and its Derivatives", Current Med. Res. and Opinion, Vol. 6, Table IV, pg 24 (1979), report a calculated probable dosage for dyphylline to produce 40 and 90 mcg/ml of dyphylline in blood for humans when given intravenously as a dose per day per 70 kg person and found it to be 13.7 and 30.8 gm respectively. Further, Zuidema et al. used the data of Svedmyr to calculate that 90 mcg/ml of dyphylline in blood would be the lowest therapeutic response toxic level in steady state. After considering intravenous use as above, these same authors, Zuidema et al., "N-substituted Theophylline Derivatives", Am. J. Hosp. Pharmacy, Vol. 37, pp 169–170 (1980) stated that dyphylline has no place in the therapy of asthmatic patients.

In fact, the majority opinion of recently published reports dealing with the use of dyphylline to treat bronchopulmonary insufficiency is that dyphylline is not a useful drug. Bussey wrote "dyphylline has no place in the therapy of bronchospasm" in 1981. Lewis indicated that dyphylline should be deleted from hospital formularies. Hendeles et al. in 1977 and 1980 stated that the therapeutic choice between dyphylline and theophylline is clear [in favor of theophylline]and that dyphylline has no place on hospital drug formularies.

Etophylline ($\beta$-hydroxyethylthophylline) is used as a bronchodilator and its pharmacokinetics have been reported by Zuidema et al., in "Pharmacokinetics of etophylline after intravenous and oral administration to humans", Int. J. Clin. Pharmacol., Therapy and Toxicol., Vol. 19, No. 7, p 310–313 (1981). The drug was given intravenously as 200 mg in 10 ml aqueous solution over 5 minutes. The authors conclude that the use of etophylline is unrealistic based on their research and knowledge of routes of administration of etophylline.

Sharma et al. reported ("Comparative bioavailability of sustained-release and conventional tablets of hydroxyethyltheophylline in man", Int. J. Clin. Pharmacol. and Biopharmacy, Vol. 17, No. 9, p 394–396 (1979)), that hydroxyethyltheophylline was useful as a sustained release dosage form to release theophylline. Later, Merkus et al., "Theophylline and hydroxyethyltheophylline are different drugs", Int. J. Clin. Pharmacol., Therapy and Toxicol., Vol. 18, No. 2, p 97 (1980) pointed out that the Sharma et al. data and conclusions were erroneous.

Acephylline (1,3-dimethylxanthinylacetic acid) is an N-7 substituted theophylline which has been given intravenously and orally (Zuidema et al., "Is Acephylline a Theophylline Bronchodilator", The Lancet, June 17, p 1318–1319 (1978)). The authors conclude that acephylline is not absorbed orally and that theophylline should be preferred as a bronchodilator.

Zuidema with others (Ufkes et al., "Efficacy of Theophylline and its N-7-Substituted Derivatives in Experimentally Induced Bronchial Asthma in the Guinea-Pig", Arch. Int. Pharmacodyn., Vol. 253, p 301–314 (1981)) have also reported that acephylline is ineffective against mediator-induced broncoconstriction in guinea-pigs, and its therapeutic value in asthmatics is doubtful. This study also found that diprophylline (dyphylline) was about 0.09 times the activity of theophylline based on effective plasma drug concentrations which agrees with other reported findings for in vitro human bronchial muscles (Svedmyr, "The Role of the Theophyllines in Asthma Therapy", Scand. J. Resp. Dis., Vol. 101, Suppl., p 125–137 (1977); Svedmyr et al., "A Comparison Between Effects of Aminophylline, Proxyphylline and Terbutaline in Asthmatics", Scand. J. Resp. Dis., Vol. 101, Suppl., p 139–145 (1977) which reported that diprophylline has 1/9 the activity of theophylline).

Ufkes et al. also report the activity of proxyphylline as 0.31 times theophylline, and etophylline as 0.44 times theophylline. These findings are all consistent with the large majority of the teachings of the literature but not with the few reports that dyphylline has a minimum effective concentration in humans in plasma of 12–16 mcg/ml (as cited earlier herein) which is about equal to theophylline's effective plasma concentrations of 10–20 mcg/ml. These differences are confusing in terms of planning therapy with N-7-substituted theophylline compounds, and the majority of reports suggest, as least indirectly, that N-7-substituted theophyllines, such as dyphylline, should not be administered in effective doses, since they are so much higher than approved doses.

Propyphylline (7-$\beta$-hydroxypropyl-theophylline) has been used and studied as a bronchodilator as discussed in Graffner et al., "Pharmacokinetic studies on proxyphylline administered intravenously and orally to man", Acta Pharmaceutica Suecia, Vol. 10, No. 6, p 425–434 (December 1973); Palmer et al., "Comparison of Drugs for Asthma", British Med. J., p 727 (March 1971); Tivenius, "Comparison of Drugs for Asthma", British Med. J., p 773 (June 1971); Selvig, "Metabolism of Proxyphylline in Man: Urinary Excretion of Proxyphylline and Its Metabolites", Drug Metabolism and Disposition, Vol. 10, No. 3, p 291–292 (1982); Selvig et al., Metabolism and Disposition, Vol. 8, No. 6, p 456–462 (1980).

In all the above cases, the N-7-substituted theophylline compounds were administered alone (with no other methyl xanthine compounds), and all intravenous doses were fairly slow, being infused over 5 minutes or longer except for Gaffner et al., who infused substantially less than an effective dose of proxyphylline over two minutes in one case.

Zuidema et al. stated, in their 1980 article, that "neither dyphylline or acefyllin nor any of the other N-substituted theophylline derivatives has a place in the therapy of asthmatic patients". This is a statement of great importance because it comes from prestigious researchers in this field. Even those of the minority view, i.e. those that believe N-7-substituted derivatives of theophylline are useful, see toxicity problems. Lawyer, et al., reported administration of dyphylline intravenously to a single patient by infusing the total dose gradually over a period of ten to thirty minutes to avoid toxicity. The one patient had separately received aminophylline; but time was allowed between doses such that the body was essentially cleared of all theophylline before the glyphylline was administered. This procedure is consistent with conventional wisdom which teaches that to administer dyphylline rapidly or to give dyphylline to a patient with theophylline in the body is likely to produce toxicity. The literature teaches that for dosing with aminophylline or theophylline that loading and maintenance doses must be reduced if the patients have been receiving any theophylline-related drugs by virtue of their inherent (and assumed additive) toxicity. Such a reduction would be anticipated to be necessary if theophylline were to be used with drugs such as dyphylline, etophylline, proxyphylline and acephylline, even though such substances are not converted to theophylline in the body. *Physicians Desk Reference*, 35th Ed. (1981), states on page 1026 that dyphylline should not be administered concurrently with other xanthine preparations. This contraindication is to prevent additive or synergistic toxicity with theophylline or structurally similar compounds.

Some methylxanthine combination drug products are known. One report, Boardman, "Interactions between theophylline and theophylline derivates in producing relaxation of guinea-pig tracheal chains", *Proceedings of the B.P.S.*, 9th–11th (April 1980), p 120–121, states that combinations of methylxanthines act synergistically in isolated guinea-pig tracheal chains to relax the muscles. No toxicity data were reported, but it could also be expected to be additive or synergistic as discussed elsewhere herein.

*Unlisted Drugs*, Vol. 28, No. 10 (October 1976), p 178, lists Neo-Biphyllin as suppositories and slow release tablets wherein: "each suppository contains: dyphylline, 187 mg.; proxyphylline, 188 mg.; and theophylline, 125 mg.; also as slow-release tablets" and Neobiphyllin (Neo-Biphyllin) is in *Unlisted Drugs*, Vol. 31, No. 4 (April 1979), p 58, wherein: "each slow-release dragee contains: proxyphylline 112.5 mg.; dyphylline, 112.5 mg.; and theophylline, 75 mg.; each suppository: 188 mg.; 187 mg.; and 125 mg.; each ampule IM, IV, or SC injectable solution; 120 mg.; 120 mg.; and 80 mg.; or 300 mg.; 300 mg.; and 200 mg." This product is said to be made by Seeback, Zurich or H. Trommsdorff, Alsdorf. The listing is quite strange since SC (subcutaneous) administration would require unrealistic volumes. If the IV (intravenous) dosage form really is available rather than being a typographical error, it would have to be administered very cautiously and very slowly as discussed in *FDA Drug Bulletin*, Vol. 10 (1980), p 4–6. Also, these listed products contain far less than normally effective doses of each of the active ingredients, even in the highest concentrations used. Undoubtedly, this is to avoid combination toxicities.

Methylxanthine combinations have been studied in people as reported in the foreign literature; Bracher et al., "Pharmakokinetic and Klinische Wirksamkeit Rektal Verabreichter Theophylline", *Respiration*, Vol. 43, p 458–466 (1982); Werdermann et al., "Zur bronchodilatatorischen Wirkung von Methylxanthin-derivaten", *Deutsche Medizinische Wochenschrift*, Vol. 104, No. 37, p 1307–1311 (September 1979); Joos et al. "Gekreuzter Doppeltbindversuch mit Neophyllin oral (Proxyphyllin und Diprophyllin) bei Asthma bronchiale", *Schweiz. Med. Wschr.*, Vol. 109, No. 19, p 726–731 (1979). Bracher et al., as well as Werdermann et al., found that by combining theophylline, dyphylline and proxyphylline, it was possible to elicit a physiological response. However, in both cases the plasma concentration of dyphylline was very low (less than 3.0 mcg/ml), as was proxyphylline (less than 9.0 mcg/ml). The rate of drug concentration increase in the plasma was quite slow, with maximum values occurring about 120 minutes after drug administration. Joos et al. reported that with plasma concentrations of about 13 mcg/ml each for dyphylline and proxyphylline, that only proxyphylline caused bronchodilation and it took 90 minutes post dosing to achieve these plasma concentrations. They did not dose the N-7-substituted theophylline derivatives in sufficient amounts in the presence of theophylline to obtain significant plasma concentrations of the N-7-substituted theophylline derivatives.

All of the above is consistent with conventional wisdom which dictates that methyl-xanthine bronchodilators should not be dosed to produce very rapid peak plasma concentrations and should not be combined with theophylline in amounts which produce individually effective concentrations.

Since aminophylline is so widely used and routinely taken by patients, and since it is contraindicated to use theophylline or a salt thereof together with other methyl xanthine preparations in normally individually effective doses. One would therefore assume that methyl xanthine drugs, such as dyphylline, etophylline and proxyphylline, should not be given in usual or normal doses or larger than previously used doses, especially intravenously, to patients who present at a hospital in acute bronchopulmonary insufficiency. Faced with such a situation, a prudent physician knowing the reported cumulative toxicity of methyl xanthine preparations, would not administer dyphylline, etophylline or proxyphylline intravenously or by any other route. The physician would anticipate potential toxicity with probable theophylline presence, would not know the necessary therapeutic concentration, and would not know with any accuracy the volume of the central compartment or the total volume of distribution of the methyl xanthines when present simultaneously in the body.

Further, both theophylline and its derivative, dyphylline, are known to penetrate the central nervous system, to infiltrate heart tissue and to distribute to lung tissue. Such structurally similar drugs which penetrate the same tissues may be expected to displace each other from some binding sites which would affect the total volume of distribution for the displaced drug. If the volume of distribution were affected such that the plasma concentration of free drug increased, then an increased toxicity could be anticipated. For example, if a subject had received a large but nontoxic, dose of theophylline, and a substantial dose of a derivative such as dyphylline was subsequently administered, it would be expected that dyphylline molecules would displace some of the bound theophylline, thereby increasing the plasma concentration of theophylline to a dangerous level. Thus, a prudent practitioner would not administer a methyl xanthine preparation, even though such a preparation might be effective in treating the acute bronchopulmonary insufficiency. And, if it was felt that the insufficiency could be relieved safely by the administration of a methyl xanthine, theophylline would be used.

Acute bronchopulmonary insufficiency usually requires immediate and rapid treatment. Intravenous aminophylline, a source of theophylline, is one of the main drugs of choice but attempts to rapidly attain therapeutic concentrations may result in toxicity including death due to the drug as described above. N-7-substituted derivatives of theophylline, such as dyphylline, have not been recommended for rapid intravenous administration.

Conventional wisdom dictates that a methyl xanthine compound, such as aminophylline, should be infused slowly, i.e. over twenty minutes as a loading dose and then reduced at the end of twenty minutes. It has been expected that the loading dose itself should be reduced or eliminated for patients who already have been taking methyl xanthine preparations. Furthermore, it has been stated that the reduced dosage schedule should be different and specific to each of the following: healthy nonsmoking adults, older patients, patients with cor pulmonale, patients with congestive heart failure, or patients taking erythromycin, triacetyl oleandomycin, lincomycin (*Physicians Desk Reference*, 35th Ed., pg 1639; Current Medical Diagnosis and Treatment, pg. 113).

Isaksson et al., as described in the references mentioned above, administered dyphylline intravenously to humans, but their data do not allow determination of the volume of the central compartment for dyphylline. Zuidema et al., *Pharmaceutisch Weckblad* (1981), report dosing 400 mg of dyphylline intravenously in humans but do not report the dosing time or the volume of the drugs central compartment. Plasma concentrations of about 48 mcg/ml are reported for only a very short time with no adverse effect.

Lawyer, et al., administered dyphylline intravenously in a patient over a ten minute period which produced peak plasma dyphylline concentrations of 17.4 mcg/ml. They report an initial distribution volume of 26.2 liters in a 37 year old woman, whose weight was 73 kg. The total or steady state volume of distribution was 32.1 liters. Only forty-four percent of the intravenous dyphylline was accounted for in the urine.

These results differ somewhat from findings obtained by compartment analysis of published oral dyphylline data as described in Gisclon et al. According to those findings, the total volume of distribution for subjects averaging a weight of 77.0 kg assuming a two-compartment open model averaged about 67 liters and the central compartment averaged about 52 liters, assuming complete bioavailability. The values reduce to about 56 liters and 44 liters respectively if bioavailability is assumed to be 84 percent. The values are such that Vc is about 0.68 L/kg and Vd total is about 0.87 L/kg for total bioavailability, while Vc is about 0.6 L/kg and Vd is about 0.73 L/kg for 84 percent bioavailability.

Simons, et al., *Allergy and Clin. Immunol.* (1975) report the pharmacokinetics of dyphylline from seven different doses in seven patients and treat dyphylline as a one-compartment drug which means that Vc would be equal to Vd total since only one compartment is involved. This is, however, inconsistent with the data reported in the above-mentioned articles by Lawyer et al. Also, the data of Simons et al. (1975) can be used to generate the following lists wherein the estimated total volume of distribution of dyphylline (total Vd) is calculated from data presented by using the equation $Vd = Dose/(K_{el})(AUC)$:

| Dosage Form | Total Vd (l/kg) |
| --- | --- |
| 5 mg/kg intramuscular | 0.58 |
| 10 mg/kg intramuscular | 0.80 |
| 5 mg/kg tablet | 0.58 |
| 10 mg/kg tablet | 0.72 |
| 10 mg/kg aqueous | 0.93 |
| 10 mg/kg alcoholic solution | 0.98 |
| 10 mg/kg alcoholic solution with glycerol-guaiacolate solution | 0.77 |

This data is quite confusing since in a cross-over study with the same patients the Vd should be constant, yet varies from 0.58 to 0.98 L/kg. The data does not allow calculation of Vc or determination of the half-life for the distribution phase only, since no distribution phase is assumed. All of this makes it impossible to propose a reasonable intravenous loading dose for dyphylline. These data, along with the analysis of the Gisclon, et al. data discussed above, teach that the data of Lawyer et al. should not be used to calculate doses for rapid intravenous dosing of patients followed by a zero-order infusion since a factor error of 2.5 times could be made in dosing based on the range of Vd values. This could be extremely important if one wished to dose dyphylline to achieve plasma concentrations of 35-40 mcg/ml or to treat a patient in an emergency room without knowing whether or not the patient had been receiving theophylline.

In summary, the present procedures for the treatment of bronchopulmonary insufficiency with a methyl xanthine are inadequate, particularly in an emergency situation. Using theophylline or one of its salts or derivatives, it is expected that one must infuse the medication slowly and in limited doses to avoid toxicity. And, if the subject has recently received, or is suspected to have received prior doses of theophylline, there has been no known way to treat the subject with methyl xanthine compounds due to the risk of toxic effects.

It has now been discovered that the disadvantages previously reported can be overcome by the use of certain N-7-substituted derivatives of theophylline, specifically, dyphylline, etophylline and proxyphylline. Quite unexpectedly, it is found that total effective doses of these substances can be administered quickly, i.e. within five and in most cases less than two minutes, without creating the life threatening condition that would exist if a similar amount of theophylline were rapidly administered.

Even more surprisingly, it is now found that the listed derivatives can be administered to a subject, along with theophylline, safely to achieve a high blood concentration of methyl xanthine compounds. In particular, by administering a combination of methyl xanthine drugs according to the present invention, a physician can safely increase a subject's total methyl xanthine plasma concentration to levels well above 20 mcg/ml. This has not been possible using theophylline alone because serious toxic effects are observed as blood concentrations of theophylline increase beyond 20 mcg/ml.

As a practical example, following the method of the present invention, an emergency room physician can rapidly relieve the bronchiopulmonary insufficiency of a patient by administering a simple intravenous injection of dyphylline, etophylline, proxyphylline or some mixture of those compounds. Because these substances do not meaningfully add to the toxicy of other methyl xanthine substances, the injection is of no danger to the subject, regardless of whether the subject has previously taken theophylline.

It is therefore an object of the present invention to provide a nontoxic pharmacological treatment to obtain bronchodilation, or diuretic or myocardial effects.

It is further an object of the present invention to provide such a pharmacological treatment which can be used safely to treat a patient who has theophylline in the body.

It is also an object to provide a method wherein a pharmacologically effective substance can be administered rapidly, such as by intravenous administration, without regard to whether or not a patient has been receiving doses of theophylline-releasing drugs.

These and other objects will become apparent by reference to the following description.

DETAILED DESCRIPTION

Figure 2:
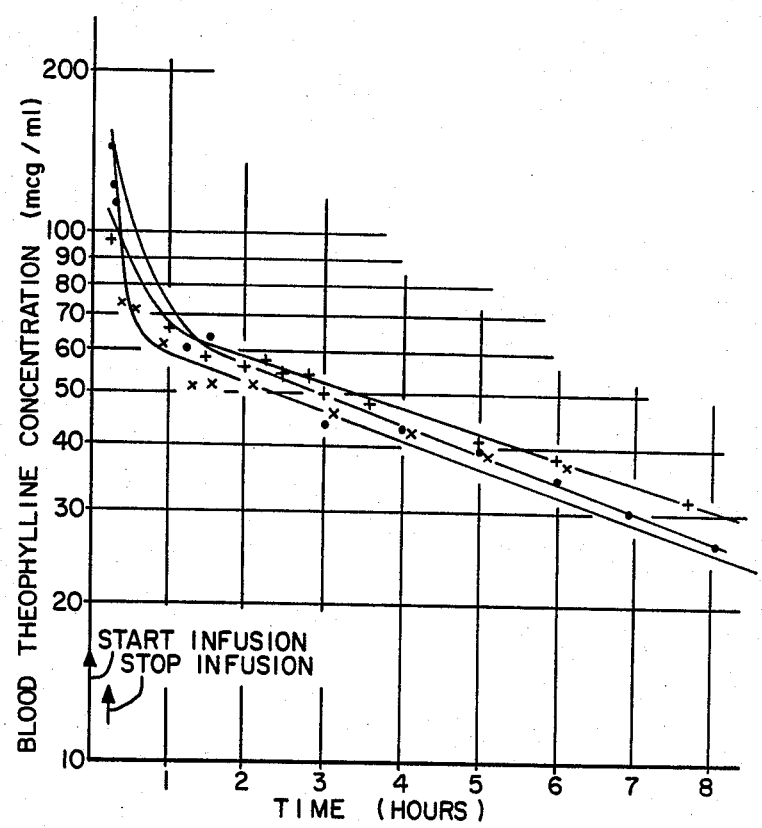
FIGS. 1-11 are graphs showing blood or plasma concentration of methyl xanthine vs. time for various test subjects.

According to the present invention, certain N-7-substituted derivatives of theophylline are administered intravenously, intramuscularly, or in the lungs, for use in combination with or in place of theophylline to obtain desirable pharmacological effects including bronchodilation, diuretic stimulation or myocardial effects. Specifically, the invention concerns the administration of dyphylline, etophylline, and proxyphylline, which are hereafter referred to as "derivative compounds" or "derivatives".

One aspect of the invention is the combined use of theophylline and one or more intravenously administered derivative compounds to benefit from the combined action of the drugs. This combination of the two drugs makes it possible to increase the total xanthine concentration in the plasma to substantially more than the xanthine concentration contribution of effective theophylline concentrations alone, without the extent of increased clinical toxicity which would be anticipated for such total xanthine plasma concentrations. Clinical toxicity refers to the occurrence of one or more toxic effects. "Toxic effects", for the purpose of this disclosure, refer to the adverse effects commonly induced by high plasma concentrations of theophylline, such effects including reduced blood pressure, restlessness, "touch sensitivity", nausea, headache, tremors, convulsions, ventricular arrhythmias, seizures, and death.

In another aspect, the invention relates to the administration of theophylline, or a theophylline salt such as aminophylline along with an intravenous administration of at least one of the derivative compounds so that the plasma concentration produced by each alone is below an effective concentration yet the combination is effective and the dose of each is reduced.

Another aspect of the invention is the intravenous use of fully effective doses of the derivative compounds to treat patients in acute respiratory distress, regardless of whether those patients have been receiving theophylline containing or releasing drugs, and without adjusting the dose of the derivatives to take into account plasma concentrations of theophylline. Such treatments are effective provided that, in a patient, the theophylline itself is at a sub-toxic level.

Still a further aspect of this invention is the rapid treatment of patients in acute respiratory distress by administering a fully effective dose of a derivative compound in a period of less than than two minutes.

A more detailed description and examples of the present invention are set forth hereinafter. It is intended that the examples be only illustrative and not restrictive, and that variations thereof may still give satisfactory results.

I. Combined Administration of Theophylline and N-7-Substituted Derivatives Thereof As discussed above, a substantial drawback of theophylline therapy is the toxicity of that compound. At high plasma concentrations, theophylline is dangerous so that dosages must be kept at a low plasma concentration, i.e. not greater than 20 mcg/ml in humans, according to the literature reports.

It has now been discovered that the effectiveness of theophylline therapy can be enhanced by administration of a derivative compound in addition to the theophylline. Quite unexpectedly, it is possible thus to increase the total methyl xanthine concentration in the plasma to levels above 20 mcg/ml, without encountering the toxicity problems one would anticipate.

The derivative and source of theophylline can be administered in the same dosage form or administered separately. And, either theophylline or the derivative may be administered by providing a suitable substance that releases the desired compound in the body.

The ability to intravenously administer a significant amount of a derivative, in addition to theophylline, was demonstrated as follows:

EXAMPLE 1

A. Introduction

1. Materials

Analytical grade chemicals were used without further purification. All water was distilled prior to use. 250 mg/10 ml aminophylline injection (Searle Laboratories, Chicago, Ill.) was diluted with an appropriate amount of distilled water for injection. Dyphylline powder (Lemmon Company, Sellersville, Pa.) was dissolved in distilled water for injection.

2. Animals

All experiments of this example were performed using female New Zealand White rabbits. These rabbits (2.4–3.6 kg) were housed in a controlled environment and allowed free access to water and food.

3. Instrumentation

A high-pressure liquid chromatographic (HPLC) system consisted of a delivery pump (M-6000A, Waters Associates, Milford, Mass.), sample injection apparatus (Model U6K, Waters Associates, Milford, Mass.), 30-cm reverse phase column ($\mu$Bondapak $C_{18}$, Waters Associates, Milford, Mass.), UV detector (Model 440, Waters Associates, Milford, Mass.) with wavelength of 280 nm and a dual pen recorder (Soltec Co., Encino, Calif.) which were used at ambient temperature.

4. Standards

Both dyphylline and theophylline stock standard solutions were prepared to contain 10, 40, 80, 120, 150, 320 or 640 mg of each in 50 ml of distilled water. 20 μl of each was then added into 0.38 ml of rabbit blood to prepare working blood standard solutions.

5. Analytical Method

The internal standard used was β-hydroxypropyl theophylline (Aldrich Chemical Co., Inc., Milwaukee, Wis.) in acetonitrile which was prepared in a 500 ml volumetric flask as a stock solution, and kept tightly sealed except during use throughout the experiment. Internal standard solution (0.4 ml) was added to an equal volume (0.4 ml) of sample to precipitate protein. After centrifuging for 10 minutes, the supernatant was injected into the HPLC. The HPLC operating conditions included a mobile phase composed of acetonitrile (6 percent V/V) in distilled water and a flow rate of 2.0 ml/min.

B. Drug Administration

Before dosing with drug the rabbit ear hair was clipped and treated with hair remover lotion (sold under the trademark NAIR, Carter-Wallace, Inc., New York, N.Y.), a catheter (Quick-Cath, 20 Ga, Travenol Laboratories, Inc., Deerfield, Ill.) and sterile intermittent infusion plug were then inserted in the rabbit's ear vein for infusion. For administration of dyphylline, the drug (250 mg/rabbit or 666.7 mg/kg) was dissolved in distilled water to make an injectable solution which was administered into a rabbit's ear vein as a continuous infusion over a period of 15 or 150 minutes using a standard infusion pump. For each separate administration of theophylline, a suitable amount of aminophylline (40 mg/kg) was dissolved in distilled water to make 10 ml injectable solution which was administered into a rabbit's ear vein as a continuous infusion over a period of 15 minutes.

Blood samples were collected from an ear vein (in the opposite ear from the infusion) at predetermined time intervals. Before collecting each sample, the rabbit ear was treated topically with xylene to dilate the ear vein for convenient sample collection. Immediately after each blood sample was drawn, 0.4 ml of blood was transfered to the centrifuge tube and 0.4 ml of acetonitrile with appropriate internal standard was added to precipitate the protein and extract drug components. After vortexing well, the blood acetonitrile mixture was centrifuged at 3000×G for ten minutes, and 10 μl of supernatant solution was then injected into the HPLC.

C. Findings

1. Dyphylline Intravenous Infusion

Figure 1:
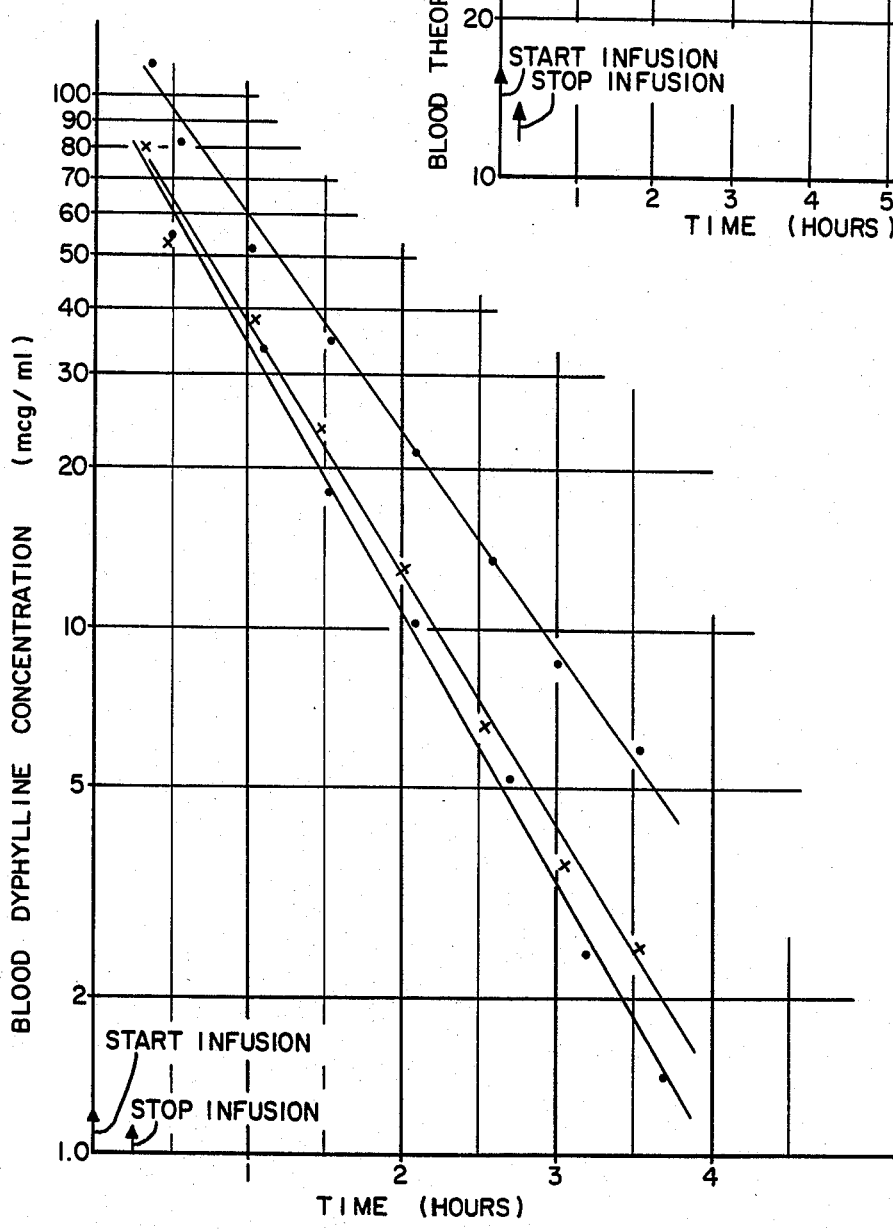

Typical log blood dyphylline concentration versus time plots, for each of the three rabbits following zero-order infusion of 250 mg over fifteen minutes are presented in FIG. 1. There is a linear decline after infusion stopped, suggesting that dyphylline distribution and elimination may be described by a standard one-compartment open pharmacokinetic model, such as the models described in Gibaldi et al., *Pharmacokinetics*, Marcel Dekker, Inc., New York (1975); and Wagner, *Fundamentals of Clinical Pharmacokinetics*, Drug Intelligence Publications, Inc., Hamilton, Ill. (1975). Parameters obtained from linear least square fitting of the terminal data to a one-compartment model appear in Table I. The fitted line of the data can be seen in FIG. 1.

TABLE I

Pharmacokinetic Parameters for Dyphylline[a] When Administered Alone.

| Rabbit | Ccut, mcg/ml[b] | Kel hr$^{-1}$ | t½ hr | Vd₁ liter/kg |
|---|---|---|---|---|
| 1 | 80.77 | 1.17 | .593 | .895 |
| 2 | 81.82 | 1.08 | .642 | .893 |
| 3 | 112.5 | .912 | .760 | .662 |
| Mean | 91.70 | 1.05 | .66 | .82 |
| S.D. | 18.02 | 0.13 | .09 | .13 |

[a]The total dose was 250.0 mg/rabbit as a zero-order infusion over 15 minutes.
[b]Blood concentration at the time the infusion of dyphylline was stopped. All other pharmacokinetic parameters are standard as defined in Wagner or Gibaldi as referenced above.

Fifteen minutes after "time zero" (the beginning of the infusion), the infusion was stopped. At that time, blood concentrations of dyphylline were about 80 to 112 mcg/ml. The rabbits did not exhibit any signs of toxicity although these concentrations are two to three times higher than the 30 to 50 mcg/ml of rabbit serum observed by Ng and Locock when lower doses were given (Ng et al., "Comparative Pharmacokinetics of Theophylline and Dyphylline Following Intravenous Injection in Rabbits", *Research Communications in Chemical Pathology and Pharmacology*, Vol. 26, pp 509–524 (1979)). This is unexpected since Ng and Locock reported surprise that 30 to 50 mcg/ml doses were not toxic to the rabbits they tested.

2. Theophylline Intravenous Infusion

A typical semilogrithmic plot of a blood theophylline concentration versus time curves, for each of the three rabbits after a zero-order aminophylline infusion of 40 mg/kg over fifteen minutes, is shown in FIG. 2. The data were fitted to a two-compartment open pharmacokinetic model with first order elimination using PROPHET (PROPHET computer system, FIT FUN routine, Director, Chemical/Biological Information Handling Program, Division of Research Resources, NIH, Bethesda, MD.) The parameters generated from three rabbits were corrected for infusion time, (as described by Gibaldi) and are listed in Table II.

TABLE II

Pharmacokinetic Parameters for Theophylline When Administered Alone.

| Rabbits | α, hr$^{-1}$ | β, hr$^{-1}$ | k12, hr$^{-1}$ | k21, hr$^{-1}$ | k10, hr$^{-1}$ | Vd, L/kg | Vel (β), L/kg | t½, hr |
|---|---|---|---|---|---|---|---|---|
| 29 | 2.748 | .121 | 1.260 | 1.366 | 0.243 | 0.279 | .562 | 5.727 |
| 30 | 8.198 | .110 | 4.547 | 3.505 | 0.256 | 0.265 | .621 | 6.3 |
| 32 | 2.923 | .010 | 1.036 | 1.826 | 0.161 | 0.360 | .576 | 6.861 |
| Mean | 4.62 | .11 | 2.28 (2.281) | 2.23 (2.232) | 0.22 (0.220) | .30 (.301) | 0.59 | 6.30 |
| S.D. | 3.10 | .01 | 1.97 | 1.13 | 0.05 | .05 | 0.03 | 0.57 |

[a]All parameters are as defined in Wagner or Gilbaldi.
[b]The total dose was 40 mg/kg of aminophylline administered as zero order infusion over fifteen minutes.

Blood concentrations of theophylline were about 110 to 130 mcg/ml when the infusion was stopped and one rabbit exhibited obvious signs of theophylline toxicity. This rabbit suffered tremors and signs of minor convulsions. The other two rabbits did not show significant signs of convulsions, but were a little "nervous and jumpy" when touched. Thus, the dose of aminophylline used caused some visible toxicity but was not lethal.

3. Fatal Toxicity of Theophylline

Aminophylline (40 mg/kg) was infused into four rabbits over fifteen minutes once every two hours until the rabbits died. After the first infusion, blood concentrations of theophylline averaged about 100 mcg/ml in all four rabbits. Although they each exhibited a different extent of "touch sensitivity," and degree of tremors, they all survived the first period of aminophylline infusion. In the second period total xanthine blood concentrations of theophylline averaged about 250 mcg/ml. Three rabbits died in this period with theophylline blood concentrations of about 250 mcg/ml. One rabbit died shortly after the third infusion which gave a blood theophylline concentration of about 400 mcg/ml. All the rabbits died following a short period of severe convulsions. The last blood sample for each rabbit was collected immediately after the rabbit died. These results are summarized in FIG. 3, wherein the last blood concentration shown corresponds to the blood sample taken at the time of death, and in Table III.

TABLE III

Blood Concentration of Theophylline When 40 mg/kg of Aminophylline was Administered as a 15 Minute Infusion Once Every Two Hours.

| Rabbit RB-1 (2.4 Kg) | | Rabbit RB-2 (3.0 Kg) | | Rabbit RB-3 (2.9 Kg) | | Rabbit RB-4 (3.0 Kg) | |
|---|---|---|---|---|---|---|---|
| Elapsed Time (hr) | Theophylline Conc (mcg/ml) | Elapsed Time (hr) | Theophylline Conc (mcg/ml) | Elapsed Time (hr) | Theophylline Conc (mcg/ml) | Elapsed Time (hr) | Theophylline Conc (mcg/ml) |
| .258 | 128.4 | .267 | 119.5 | .283 | 152.6 | .267 | 140.2 |
| .50 | 106.0 | .517 | 107.5 | .508 | 120.7 | .517 | 114.7 |
| .775 | 97.3 | .767 | 101.1 | .8 | 111.5 | .758 | 103.2 |
| 1.058 | 92.2 | 1.02 | 96.3 | 1.02 | 98.0 | 1.01 | 104.0 |
| 1.25 | 84.8 | 1.2 | 95.1 | 1.26 | 92.5 | 1.27 | 98.3 |
| 1.57 | 77.9 | 1.54 | 92.8 | 1.52 | 81.0 | 1.51 | 93.7 |
| 2.03 | 75.9 | 1.97 | 87.6 | 1.98 | 78.5 | 1.98 | 82.8 |
| 2.32 | 362.4 | 2.28 | 287.6 | 2.27 | 306.9 | 2.28 | 261.2 |
| 2.87 | 242.8 | 2.43 | 282.5[a] | 2.78 | 253.7 | 2.55 | 242.1[a] |
| 3.58 | 233.6 | | | 3.30 | 243.7 | | |
| 4.18 | 220.7 | | | 3.42 | 238.5[a] | | |
| 4.57 | 416.4[a] | | | | | | |

[a]Blood concentration of theophylline at the time of death.

4. Concurrent Administration of Theophylline and Dyphylline

Figure 4:
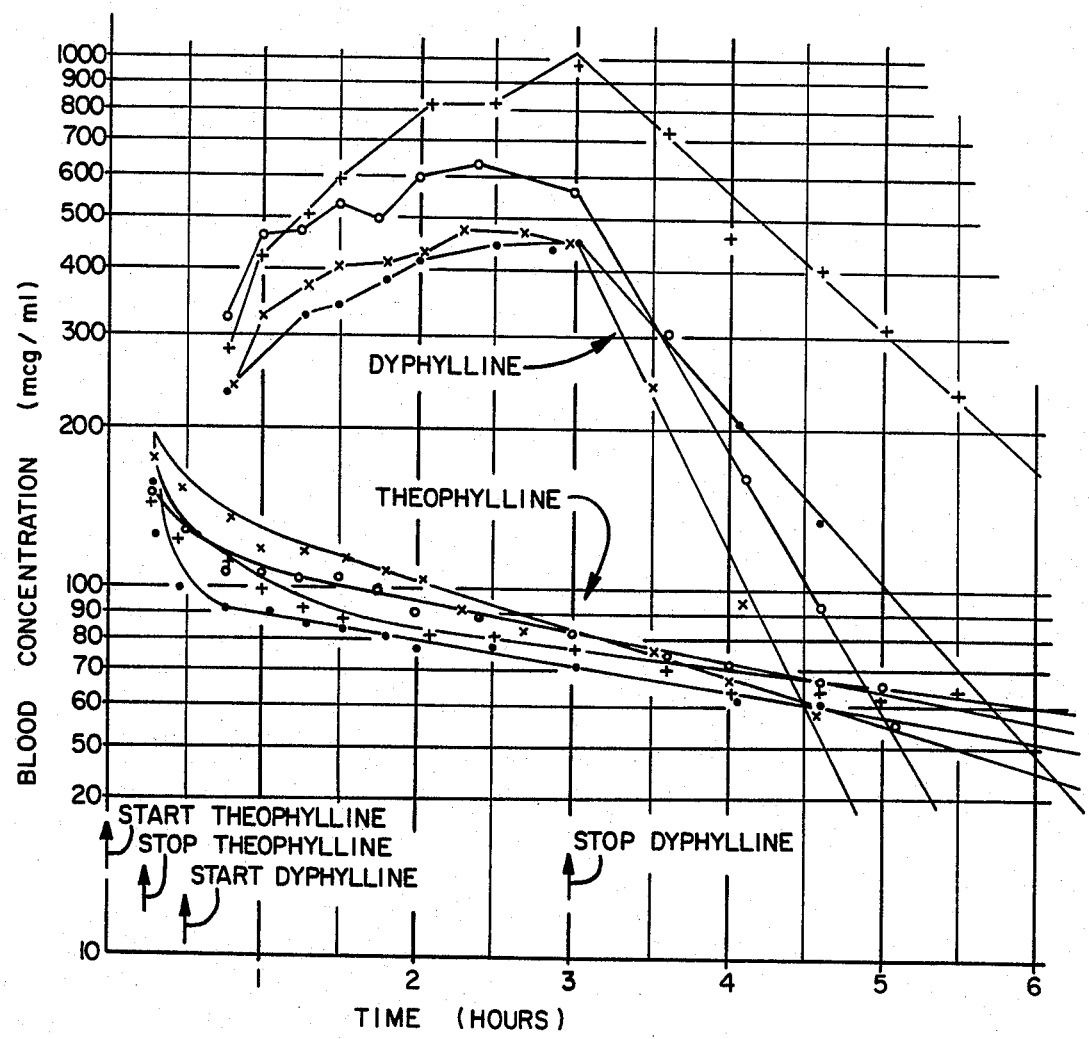

Semilogrithmic plots of post infusion data of dyphylline and theophylline when present concurrently for four rabbits are presented in FIG. 4. The plots show blood concentrations following one intravenous infusion of 40 mg/kg of aminophylline (lower curves) over 15 minutes, and a 60 mg intravenous bolus injection (less than 5 seconds) of dyphylline followed by an intravenous infusion of 666.7 μg/kg of dyphylline (upper curves) over 150 minutes. The post infusion data of theophylline were fitted to a two-compartment open model using the same procedure as described above. Although samples were collected while infusion of dyphylline was continuing, only post infusion data were used for dyphylline pharmacokinetic analysis. The microscopic constants calculated for data in FIG. 4 are in Table IV and V respectively for dyphylline and theophylline.

TABLE IV

Pharmacokinetic Parameters for Dyphylline[a] When Administered When Theophylline Was Present.

| Rabbit | Ccut, mcg/ml[b] | Kel hr$^{-1}$ | t½ hr | Vd l/kg |
|---|---|---|---|---|
| 45 | 455.4 | .743 | .933 | .664 |
| 46 | 450.4 | 1.35 | .513 | .369 |
| 47 | 976.8 | .61 | 1.136 | .283 |
| 48 | 566.4 | 1.16 | .597 | .304 |
| Mean | 612.0 | .97 | .79 | .41 |
| S.D. | 249.07 | .35 | .29 | .18 |

[a]The initial dose was 60 mg by rapid intravenous "push" administration (less than 5 seconds administration time) immediately followed by another dose of 666.7 mg/kg as a zero-order infusion of dyphylline over 150 minutes.
[b]Blood concentration at the time of infusion of dyphylline was stopped. All other pharmacokinetic parameters are standard as defined in Wagner or Gibaldi.

TABLE V

Pharmacokinetic Parameters[a] for Theophylline[b] when Administered and Followed by Dyphylline Administration.

| Rabbit | α hr$^{-1}$ | β hr$^{-1}$ | k12 hr$^{-1}$ | k21 hr$^{-1}$ | k10 hr$^{-1}$ | Vc hr$^{-1}$ | Vd(B) hr$^{-1}$ | t½ hr$^{-1}$ |
|---|---|---|---|---|---|---|---|---|
| 45 | 10.940 | .111 | 6.663 | 4.091 | 0.297 | .151 | .403 | 6.243 |
| 46 | 4.406 | .203 | 1.214 | 3.107 | 0.288 | .187 | .266 | 3.414 |
| 47 | 1.951 | .076 | .719 | 1.182 | 0.126 | .252 | .417 | 9.118 |
| 48 | 5.753 | .128 | 1.905 | 3.782 | 0.195 | .219 | .333 | 5.414 |
| Mean | 5.76 | .13 | 2.63 | 3.04 | .23 | .20 | .35 | 6.05 |
| S.D. | 3.79 | .05 | 2.74 | 1.31 | .08 | .04 | .07 | 2.37 |

[a]All parameters are standard as defined in Wagner and Gibaldi.
[b]The dose was 40 mg/kg of aminophylline administered over 15 minutes.

Figure 3:
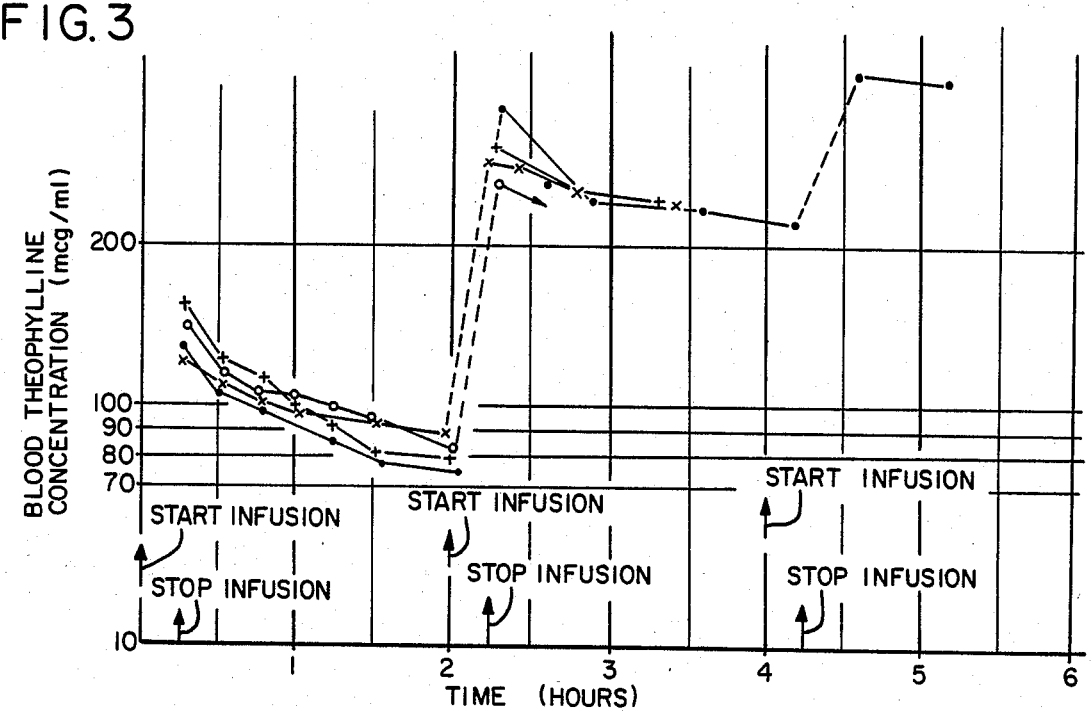

The high blood theophylline concentrations during the first two hours caused the rabbits to be "touchy" and exhibit some tremors about two hours after beginning infusion of the theophylline. These effects were qualitatively the same as when aminophylline was given alone (FIG. 2 and FIG. 3 during the first two hours). The rapid bolus injection of dyphylline followed by a concurrent infusion of dyphylline did not increase the severity of the tremors and no convulsions developed. All four rabbits survived. These experiments showed that extremely high total xanthine blood concentrations (average about 650 mcg/ml) produced no more visible toxicity than was observed as due to the theophylline alone.

These findings are quite dramatic and unexpected. Both theophylline and dyphylline are xanthines known to cause central nervous system stimulation and convulsions in high doses. The *Physicians Desk Reference*, 35th edition, states that dyphylline should not be administered concurrently with other xanthine preparations. The failure of these large doses of dyphylline and total concentrations of xanthines over about 650 mcg/ml to cause convulsions when about only 250 mcg/ml of theophylline alone causes convulsions and death is very unexpected and has extensive implications for use of these drugs together.

Therapeutically effective plasma concentrations of theophylline in humans are 10–20 mcg/ml and toxicity such as nausea, headache and restlessness often occurs when plasma concentrations exceed 20 mcg/ml. Larger concentrations may produce convulsions but there are often no early signs of the above less serious symptoms which may appear in up to 50 percent of patients prior to onset of convulsions. Ventricular arrhythmias or seizures may be the first signs of toxicity as described in *Physicians Desk Reference*, 35th edition, p. 656 (1981). Thus, if theophylline plasma concentrations are increased from 15 to 30 or 40 mcg/ml in humans, one would expect serious toxicity to occur. Also, if theophylline concentrations were 15 mcg/ml and dyphylline were present at 15 to 25 mcg/ml for a total methylxanthine concentration of 30 to 40 mcg/ml, one would expect toxicity to occur.

One might expect not only a directly additive effect but even a multiplied effect since both drugs apparently stimulate the same receptor site. Further, since one drug may be expected to affect the volume of distribution of the other as discussed earlier, one would reasonably expect that a dose of dyphylline which, when given alone, produced plasma concentrations of 30 mcg/ml, when given to a patient whose plasma concentration of theophylline was 15 mcg/ml might produce total methylxanthine concentrations of more than 45 mcg/ml with increased toxicity, i.e. that normally safe doses of each would be synergistic in toxicity.

All the above expectations are equally appropriate for rabbits as for humans. However, quite unexpectedly, the data in FIG. 4 show a lack of increased visible toxicity for such high drug concentrations. Surprisingly, as shown in FIG. 4, all the animals lived, and none entered into convulsions.

The dose of aminophylline used to generate the theophylline concentrations shown in FIG. 4 was large enough to produce visible toxic symptoms. In clinical practice, the desired doses of aminophylline or theophylline are such that no symptoms of theophylline toxicity will be deliberately produced. Therefore, if extremely large doses of dyphylline can be added to doses of theophylline which are large enough to produce visible toxicity without the dyphylline increasing the toxicity, then it is reasonable to conclude that much smaller (but independently clinically effective) doses of dyphylline can be administered to people receiving usually clinically effective doses of aminophylline or theophylline without producing toxicity. Thus, this example demonstrates that dyphylline and theophylline can be used together without producing synergistic or additive toxicity to the extent expected.

Theophylline has an average total volume of distribution in this example of about 0.59 L/kg (Table II) when given alone or about 0.35 L/Kg (Table V) when given with dyphylline. One might attribute this difference to the presence of dyphylline or to biological differences in rabbits. The data in Table V are much more variable than the data in Table II which might support the hypothesis that uncontrolled variation accounts for the difference observed rather than a dyphylline effect. Examination of the average blood concentrations of theophylline immediately after stopping the infusion (time equal 15 minutes) shows about 100 mcg/ml (corresponds to Table II data) or about 150 mcg/ml (corresponds to Table V data). These values occur prior to any dyphylline administration and might indicate that the average volume of distribution (Vd) for the rabbits of Table II is larger than the average volume of distribution of rabbits of Table V, independent of dyphylline administration.

Also, if the data from time one hour to two hours only in FIG. 3 is used to calculate the volume of distribution (Vd) for these rabbits (prior to the second infusion of aminophylline), then the Vd values are 0.37 L/kg, 0.37 L/kg, 0.32 L/kg and 0.33 L/kg for an average of 0.35 L/kg which is about the same as in Table V, which indicates that dyphylline does not affect the volume of distribution of theophylline.

FIGS. 2 and 3 show that for theophylline the distribution phase is complete at about 60 to 75 minutes, which is consistent with the theophylline data in FIG. 4. Tables II and V both show that the average half-life of theophylline is about 6 to 6.5 hours, which is consistent with the approximate half-life for theophylline estimated from the data of FIG. 3 from time 1 hour to 2 hours only. Therefore, dyphylline does not appear to alter the half-life of theophylline. Also, since the theophylline half-life has not been affected and the blood concentrations of theophylline in FIG. 4 all lie on the same line (for a given subject) during the time that dyphylline concentrations vary from about 250 mcg/ml up to and above about 500 mcg/ml and back down to about 60 mcg/ml, the dyphylline apparently did not affect the volume of distribution of theophylline. If dyphylline were affecting the volume of distribution of theophylline, then the slope of the lines for theophylline should have changed from about time one hour to about time three hours or more. For example, if dyphylline decreased the volume of distribution of theophylline by fifty percent or more, then the blood concentrations of theophylline should have increased dramatically enough during the dyphylline infusion to produce a definite effect on theophylline plasma concentrations. Such an effect did not occur as is evident by examination of FIG. 4. Thus, dyphylline did not appear to exert a significant affect on the volume of distribution of theophylline in these rabbits studied.

These findings are significant since the therapeutic range of theophylline in people is generally accepted to be about 10–20 mcg/ml of plasma. Toxicity occurs regularly at concentrations above 20 mcg/ml. Thus, the data indicate that if desired concentrations of theophylline exist, say 15 mcg/ml, then coadministration of dyphylline will not cause the theophylline concentrations to increase to over 20 mcg/ml. The exact effect of dyphylline on the volume of distribution of theophylline is not critical to the current invention since it has been shown that the drugs can be administered together without synergistic or additive toxicity to the extent expected.

The average apparent volume of distribution of dyphylline is 0.82 L/kg (Table I) for dyphylline administered alone and 0.41 L/kg (Table IV) when administered with theophylline. Ng and Locock reported an average volume of distribution of dyphylline in rabbits of 1.01 L/kg. Thus, it may be that theophylline affected the volume of distribution of dyphylline (compare Tables I and IV), or it may be that the apparent volume of distribution of dyphylline decreases as dose is increased since Ng and Locock dosed dyphylline at 25 mg/kg while the data for Table I is for about 80 mg/kg and for Table IV is 666.7 mg/kg. Gisclon et al. reported that dyphylline may bind nonlinearly to protein, and Poynor has reported that high-dose dyphylline may produce nonlinear pharmacokinetics: Wesley Jim Poynor, "Dyphylline Pharmacokinetics Following Two Consecutive Intravenous Infusions in Dogs", Ph.D. Thesis, The University of Texas at Austin, pp. IX and 165, December 1980).

Evaluation of FIG. 4 shows that the terminal log-linear phase for dyphylline is, in fact, quite linear for each subject over plasma concentration ranges of 600 to less than 100 mcg/ml. If increased concentrations (or doses) of dyphylline were producing substantially decreased total volumes of distribution for dyphylline, then the terminal log-linear phase (FIG. 4) should not be so linear, but should be convex, which is not observed. Whether or not high doses of theophylline affect the volume of distribution of high doses of dyphylline is not critical to the invention described herein since one can predict from this example that much lower doses on a mg/kg basis of dyphylline and theophylline, as used clinically, will not be toxic to the extent previously expected.

This study has been done in rabbits since it is not reasonable to dose humans with theophylline to the edge of convulsions and then dose with additional methylxanthine like dyphylline. However, the discovery that lower doses of each (on a mg/kg basis) can be present concomitantly in humans is demonstrated by the data in this example. It seems especially clear that both theophylline and dyphylline can be used together in their respective ranges of recommended effective plasma concentrations, without inducing convulsions. Some minor toxicities, such as headache or nausea, may develop in humans at these lower concentrations since these could not be evaluated in rabbits. However, such events should be rare since the major toxic symptoms were not additional or synergistic to the extent expected.

II. Rapid Intravenous Administration of N-7-Substituted Derivatives of Theophylline Infusion of a loading dose of a methylxanthine compound over twenty minutes is standard practice, but the effect is much slower than desired in a clinical setting where a patient may suffer from status-asthmaticas. Extremely rapid administration of an effective N-7-substituted derivative of theophylline, such as dyphylline, may decrease the need for the combination therapy concurrently used in such conditions. The approximate volume of the central compartment of two compartment drugs is necessary to know how to rapidly dose such drugs.

The derivative compounds can safely be administered at the most rapid rate which does not cause a build-up of fluid in the lungs of the subject. This means, in virtually every case, that sufficient derivative compound to have a therapeutic effect, and specifically an amount sufficient to produce a plasma concentration of 10 mcg/ml, can be administered in less than two minutes by I.V. bolus. Such a rapid infusion can immediately be followed by a zero order infusion of the same or a different derivative to maintain, in the body of the subject, the amount of derivative achieved by the rapidly administered dose. As an alterative, a second dose of the derivative can be rapidly intravenously administered in less than two minutes, within thirty minutes of the first dose, the second dose optionally being followed by a zero order infusion.

Data in the previous examples when combined with the example below teach the new method for treating acute bronchopulmonary insufficiency by administration of dyphylline as a rapid intravenous loading dose followed by intravenous infusions.

EXAMPLE 2

1000 mg of the drug dyphylline was infused over twenty minutes in two heathy male patients to determine the volume of distribution of the central compartment.

A physician evaluated two male volunteer subjects for their drug and disease histories. Both subjects were healthy and did not take any medication or drugs from one week before the study until its completion. The subjects fasted from 10:00 p.m. before dosing at 7:30 a.m. the following day until four hours post dosing, after which food (except xanthines; i.e. chocolate, tea, coffee) and beverages were allowed ad lib.

A dose of 1,000 mg of dyphylline (Neothylline ®) diluted in normal saline (0.9 percent) was administered at a rate of 50 mg/min via a constant infusion pump for twenty minutes. Blood pressure and electrocardiogram readings were monitored by a physician.

A heparin lock was placed in the back of the hand of each subject by an intravenous therapy nurse prior to sampling of blood.

Whole blood (7 cc) was collected from each subject at time zero just prior to dosing and at 10, 15, 20, 30, 40 minutes and 1.0, 1.5, 2.0, 3.0, 4.0, 5.0, 6.0, 7.0, 8.0, 12.0, and 16.0 hours post dosing with a syringe. The heparin lock was cleared of all heparin solution and the lock filled with subject blood by using a disposable syringe prior to sampling. Each sample was then collected in a new disposable syringe and immediately transferred to a heparinized vacuum tube. After each sampling, the heparin lock was flushed and filled with heparin (10 u/ml). Once samples had been transferred to vacuum tubes, they were inverted several times, then stored in crushed ice until centrifuged and the plasma collected. Plasma samples were then frozen until assayed.

Urine samples were collected just prior to dosing and at intervals of 0 to 2, 2 to 4, 4 to 6, 6 to 8, 8 to 16, 16 to 24, 24 to 32, 32 to 40, 40 to 48, 48 to 56, 56 to 64, and 64 to 72 hours post dosing. Subjects were provided with separate containers for each collection interval and instructed to void their bladders completely at the end of each interval. Samples were stored at 4° C. until urine volumes were recorded, then aliquots of each sample were frozen until assayed.

Plasma and urine samples were assayed by high-pressure liquid chromatography (HPLC) as reported by Gisclon, in the article mentioned above.

Plasma samples were prepared for assay by mixing 0.5 ml of plasma with 0.5 ml of acetonitrile containing β-hydroxyethyltheophylline (40 mcg/ml) as internal standard, and vortexed 15 seconds. The plasma sample with its protein precipitate was then centrifuged for 15 minutes at 2800 rpm and 5-40 μl injected into the HPLC.

Urine samples were extracted prior to injection into the HPLC. Each urine sample (0.5 ml) was mixed with 0.5 ml of β-hydroxypropyltheophylline at a concentration of 35 mcg/ml in acetonitrile, and vortexed for 15 seconds. The sample was passed through a resin column which selectively attaches water soluble organic molecules such as dyphylline. Dyphylline was washed from the column using 15 ml isopropanol-chloroform (1:3) mixture which was collected in a test tube containing 1 ml 0.2 N NaOH, and centrifuged for fifteen minutes. The aqueous layer was removed by aspiration and the organic layer evaporated to dryness with a nitrogen stream in a water bath at 55° C. The sample was reconstituted with 1.0 ml of methanol and 5-40 μl injected into the HPLC.

Figure 5:
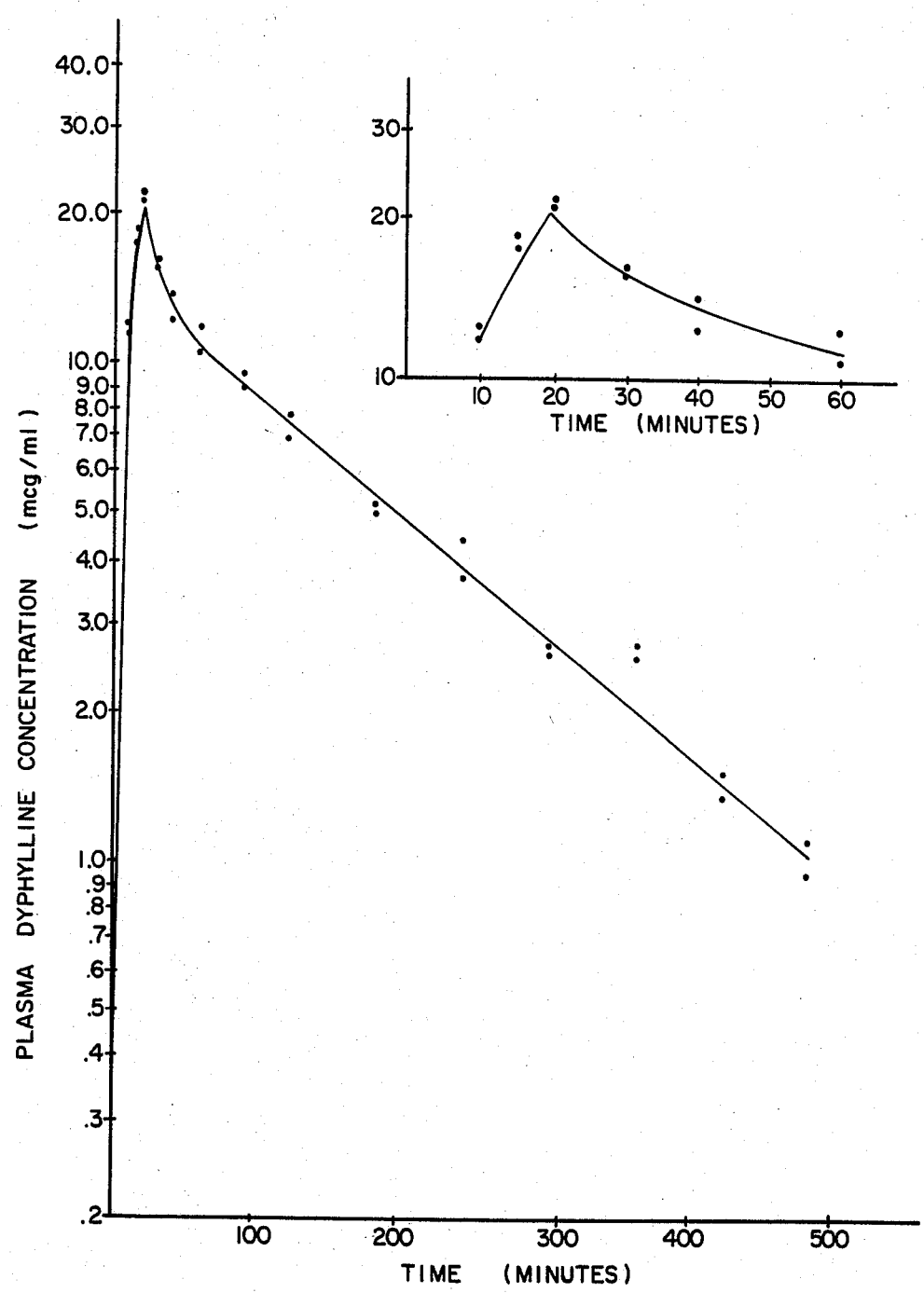
Figure 6:
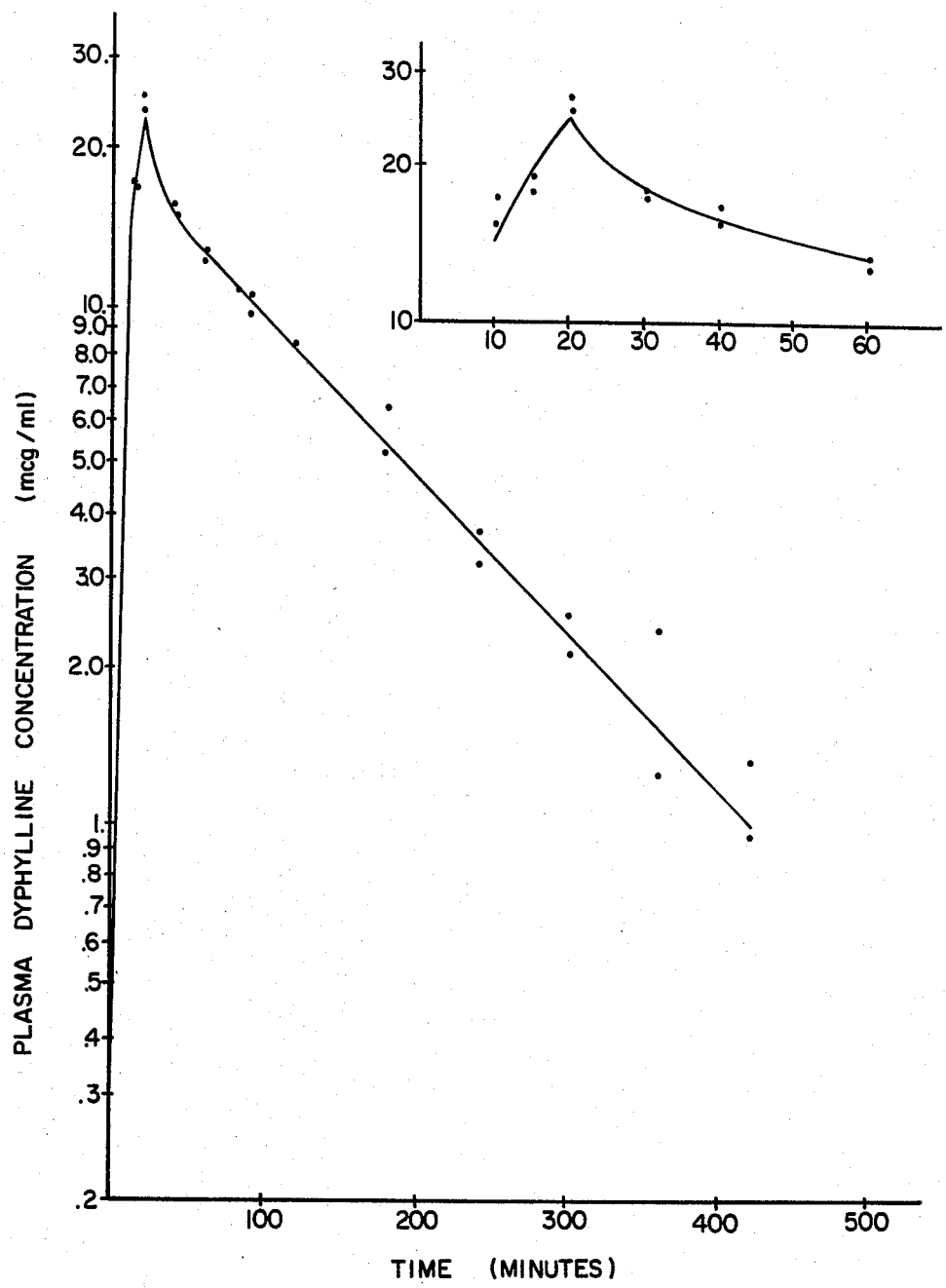

FIGS. 5 and 6 show dyphylline plasma concentration vs. time curves for the subjects. Solid circles are the data points which were obtained by duplicate analysis of each sample by different analysts and the solid line represents the predicted values obtained after fitting the data with an Autoan computer package which uses CSTRIP and NONLIN (John G. Wagner, *Fundamentals of Clinical Pharmacokinetics,* Drug Intelligence Publications, Inc., Hamilton, Ill., 1975). This program determined that the data from time zero to 480 min. (8 hr) for subject one and 420 min. (7 hr) for subject two were compatible with a two compartment open model with zero order infusion for 20 minutes and first order elimination from the central compartment only. The fit to the data was quite good with $r^2=0.996$ for subject one and 0.997 for subject two. The average percent deviation for the predicted lines from the data points was 7.7 percent and the estimated concentrations averaged 98.9 percent of the observed concentrations. Table VI shows the estimated pharmacokinetic parameters for the subjects.

TABLE VI

Dyphylline Pharmacokinetic Parameters[a] Obtained After Intravenous Infusion (20 min.) of 1000 mg in Two Human Subjects.

| Parameters | Subject 1 | Subject 2 |
|---|---|---|
| $K_{21}$ (hr$^{-1}$) | 2.50 | 4.39 |
| $K_{el}$ (hr$^{-1}$) | 0.62 | 0.84 |
| $K_{12}$ (hr$^{-1}$) | 1.94 | 4.02 |
| α (hr$^{-1}$) | 4.73 | 8.83 |
| β (hr$^{-1}$) | 0.33 | 0.42 |
| t½ (hr)[b] | 2.11 | 1.66 |
| Css (mcg/ml)[c] | 142.56 | 142.13 |
| $V_1$ (L) | 33.93 | 25.15 |
| $V_2$ (L)[d] | 30.28 | 25.45 |
| $V_3$ (L)[e] | 64.21 | 50.60 |

[a] Calculated by Autoan assuming first order elimination with 1/y2 weighting.
[b] Half-life = 0.693/β
[c] Css, steady state = infusion rate/$V_1 K_{el}$ (predicted only, not obtained by establishing Css)
[d] $V_2$, Volume of peripheral compartment = $V_d - V_1$
[e] $V_d$, total volume of distribution = $(K_{el})(V_1)/β$
Note:
Each value is obtained by Autoan fitting of the plasma values obtained by fitting all results of analyst one and analyst two for each sample.

Table VII shows subject characteristics and Table VIII shows blood pressure and pulse rate data before, during, and after drug infusion. Although the maximum recorded systolic blood pressure occurred at maximum plasma drug concentration, the effect was small. Blood pressure as well as pulse rate were essentially unchanged during the study. No adverse side effects were observed or reported.

TABLE VII

| | Subject Characteristics | | | | |
|---|---|---|---|---|---|
| | Race | Sex | Age | Weight | Height |
| Subject One | Caucasian | Male | 31 yrs. | 72.7 kg, 160 lb | 5'11", 1.80 M |
| Subject Two | Caucasian | Male | 30 yrs. | 70.5 kg, 155 lb | 6'02", 1.88 M |

[a] Neither subject had any known disease, chronic or acute.
Neither subject was taking any medication other than OTC products which (along with alcohol) were not taken from one week prior to the study until the study was completed.
Neither subject had any known allergies or history of allergies.

TABLE VIII

Subjects' Blood Pressure and Pulse Rate

| SUBJECT ONE[a] | | | SUBJECT TWO[b] | | |
|---|---|---|---|---|---|
| Time | Pulse[c] | BP[d] | Time | Pulse | BP |
| 0650 | 54 | — | 0645 | 77 | — |
| 0710 | 70 | — | 0710 | 63 | — |
| 0715 | 60 | 120/75 | 0715 | 65 | 125/80 |
| 0720 | 57 | — | 0720 | 67 | — |
| 0725 | 54 | — | 0742 (10 M)[e] | 76 | 120/80 |
| 0740 (10 M)[e] | 56 | 110/75 | 0747 (15 M) | 66 | 120/85 |
| 0745 (15 M) | 58 | 115/75 | 0752 (20 M)[f] | — | 130/80 |
| 0750 (20 M)[f] | 57 | 125/75 | 0802 (30 M) | 66 | 120/80 |
| 0800 (30 M) | 55 | 115/70 | 0812 (40 M) | 67 | 120/80 |
| 0810 (40 M) | 61 | 120/80 | 0832 (60 M) | — | 115/80 |
| 0830 (60 M) | 53 | 105/70 | 0902 (90 M) | 62 | 115/75 |
| 0900 (90 M) | 61 | 105/70 | | | |

[a] Time zero (start of infusion) for Subject One is 0730.
[b] Time zero (start of infusion) for Subject Two is 0732.
[c] Pulse rate (beats/minute) read from electrocardiogram via a Cardiac Nomogram Ruler (manufactured by Lilly 60-MJ-7852-0) using two cycles.
[d] Blood pressure, mm Hg, obtained via blood pressure cuff.
[e] Minutes after the start of the infusion.
[f] Dyphylline plasma concentration peaks at twenty minutes which is the time the infusion stopped.

The volume of the central compartment was about 25 to 34 liters or about 0.35 L/kg to 0.47 L/kg for an average of about 0.41 L/kg and the total volume of distribution averaged about 0.80 L/kg for the two subjects.

Thus, the data in this example combined with the previous example suggests a new method of use of dyphylline, wherein the drug can be administered as a bolus injection over only a short time period, such as two minutes at a dose of about 15-20 mg/kg, which would produce a peak plasma concentration of about 35 to 50 mcg/ml. Zero-order intravenous infusion could be started simultaneously to maintain desired plasma concentrations of drug. As further data become available so that "average" central compartment volume and total volume of distribution for dyphylline are more precisely established, it will be possible more precisely to propose a dose. Such a dose might be more or less than stated herein but could be given as a bolus injection.

Doses of the size indicated herein are not likely to be toxic since 100 mcg/ml of dyphylline is not toxic in dogs and much higher concentrations are not toxic in rabbits. Example 1 teaches that plasma concentrations of about 600 mcg/ml of dyphylline in the presence of theophylline concentrations of about 100 mcg/ml are not toxic to rabbits. Thus, the dyphylline can be administered rapidly intravenously regardless of whether or not the patient has been taking theophylline releasing drugs, providing the theophylline itself is not at a toxic level.

The dyphylline administered by "bolus" injection will be cleared from the central compartment with a half-time of about around four to nine minutes (see Table I) which means that a second loading "bolus" dose of about one-half as much as the first dose may be given ten minutes after the first dose and a zero-order infusion can be started. Lower doses can certainly be used if the drug is effective at less than about 30 mcg/ml concentrations.

EXAMPLE 3

Figure 7:
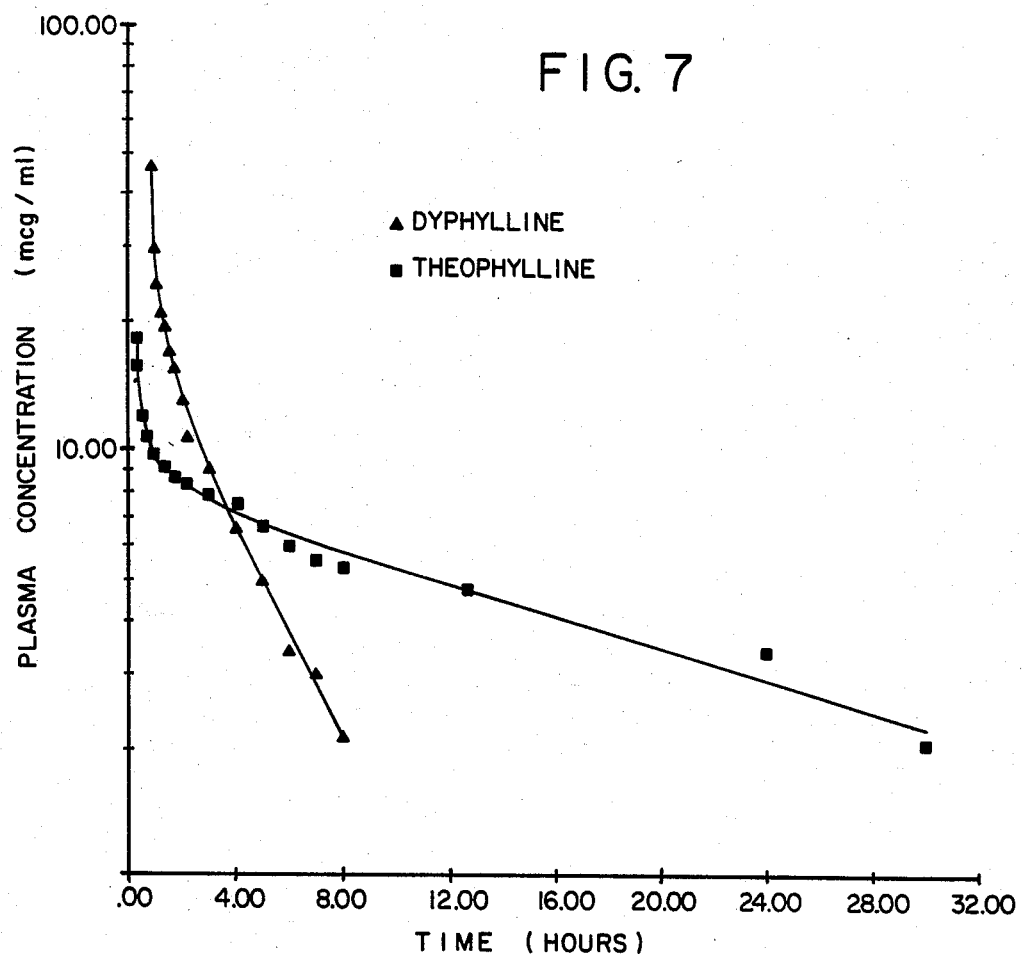

Two horses were administered dyphylline and aminophylline concomitantly. The first horse received an intravenous infusion (10 mg/kg of aminophylline dissolved in one liter of D5W) over 17 minutes into the jugular vein. 23 minutes after the infusion stopped or 40 minutes post time zero, a bolus injection (20 mg/kg) of dyphylline (100 mg/ml in D5W) was administered into the jugular vein over 15 seconds. FIG. 7 shows the plasma concentrations for both drugs.

Figure 8:
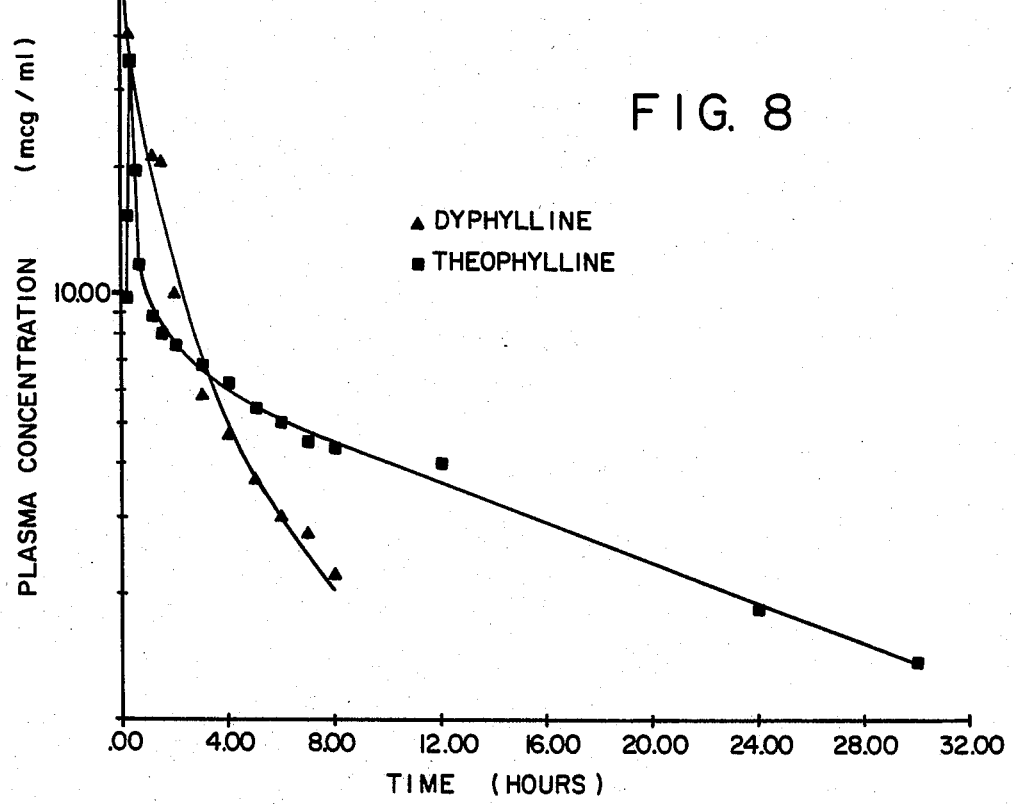
Figure 9A:
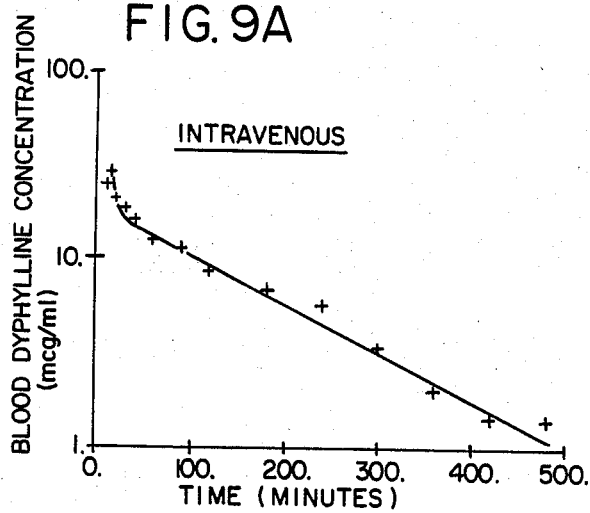
Figure 9B:
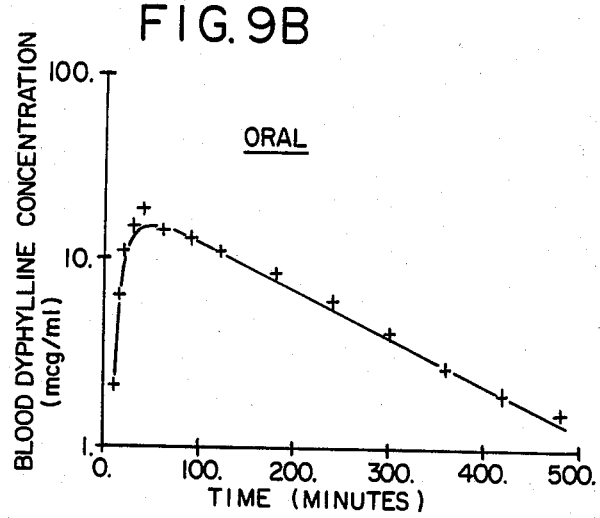
Figure 10A:
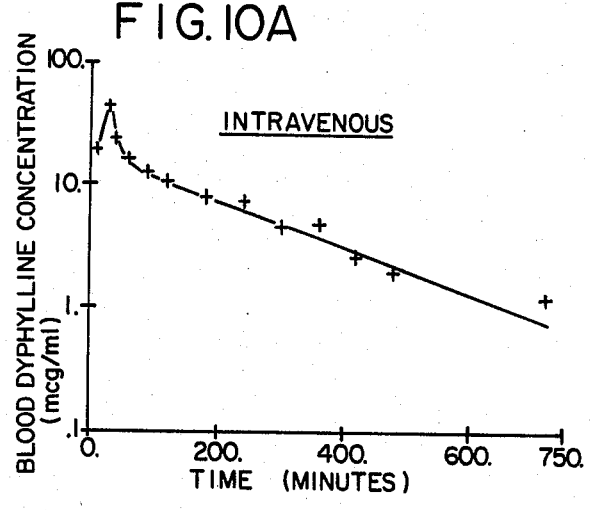
Figure 10B:
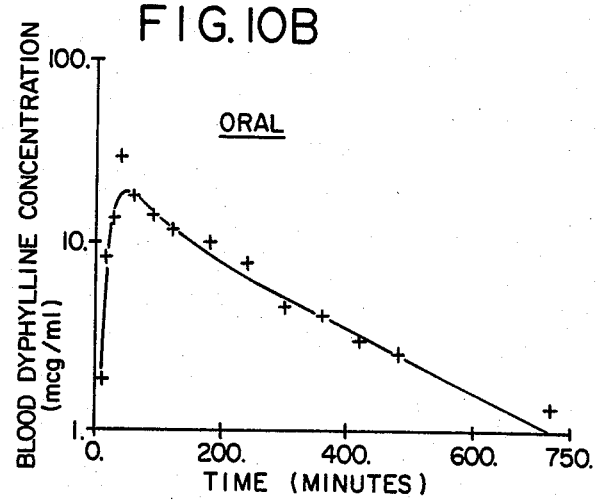
Figure 11A:
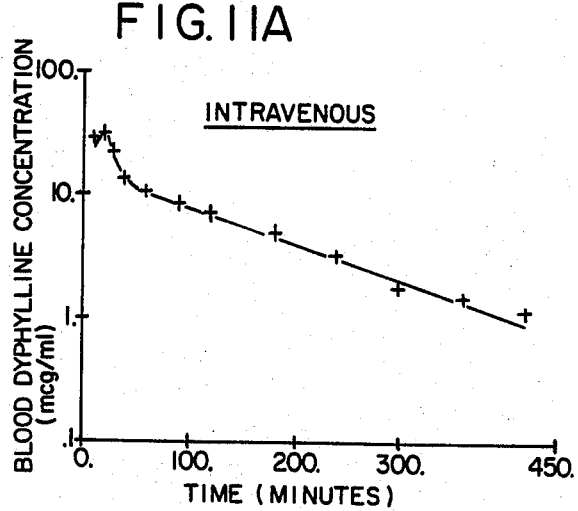
Figure 11B:
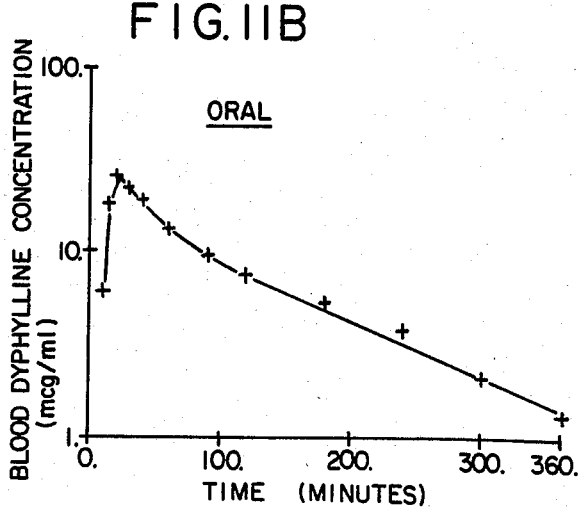

The second horse was given a bolus injection of dyphylline (20 mg/kg as 100 mg/ml solution in D5W) over 15 seconds into the jugular vein. Aminophylline infusion (10 mg/kg dissolved in one liter of D5W) was started immediately and administered over 20 minutes. Plasma concentrations of both drugs are shown in FIG. 8.

The peak plasma concentration values of theophylline were 18 and 35 mcg/ml respectively. Dyphylline peak plasma concentrations measured were 46 and 88 mcg/ml. Total methylxanthine concentrations were about 55 to 110 mcg/ml. There were no apparent toxicities associated with these high plasma concentrations of total methylxanthine as produed by rapid bolus injection of dyphylline to horses also receiving aminophylline. After the first day of the study was completed, the grooms brushed out the horses and noticed that they had been sweating, as the hair was matted and stringy.

Table IX shows the blood pressures and pulse rates for the two horses.

TABLE IX

Physiological Parameters in Two Horses Following Intravenous Aminophylline and Dyphylline

| Elapsed Time (minutes)[1] | | Blood Pressure | | |
|---|---|---|---|---|
| Post Aminophylline | Post Dyphylline | S/D | Mean | p[2] |
| Horse 1 | | | | |
| 0 | | 156/98 | 119 | 42 |
| 10 | | 150/83 | 106 | 44 |
| 20 | | 222/117 | 156 | 60 |
| 30 | | 180/90 | 123 | 56 |
| 40 | 0 | 214/119 | 148 | 56 |
| 50 | 10 | 162/93 | 116 | 48 |
| 60 | 20 | 130/90 | 117 | 48 |
| 70 | 30 | 166/86 | 108 | 48 |
| 80 | 40 | 176/88 | 113 | 44 |
| 90 | 50 | 158/82 | 108 | 46 |
| 100 | 60 | 160/90 | 120 | 46 |
| 120 | 80 | 156/87 | 106 | 46 |
| 130 | 90 | 162/97 | 115 | — |
| 180 | 140 | 150/82 | 102 | 48 |
| 240 | 200 | 154/88 | 110 | 44 |
| Horse 2 | | | | |
| 0 | | 161/91 | 113 | 38 |
| 10 | | 147/75 | 99 | 40 |
| 20 | | 148/78 | 96 | 50 |
| 30 | | 150/69 | 92 | 40 |
| 40 | | 134/63 | 87 | 58 |
| 60 | | 135/67 | 85 | 38 |
| 90 | | 131/62 | 80 | 40 |
| 120 | | 140/68 | 82 | 40 |
| 180 | | 138/70 | 86 | 40 |
| 240 | | 150/71 | 93 | 36 |

[1]Horse 1 received aminophylline (10 mg/kg) infused over 20 minutes and then 40 minutes post time zero a dose of 20 mg/kg dyphylline was given as an IV bolus over 15 seconds. Horse 2 received 10 mg/kg dyphylline IV bolus over 15 seconds and aminophylline (10 mg/kg) started at time zero and infused over 20 minutes.
[2]Pulse (beats per minute).
[3]Respirations per minute.

In both horses, the pulse increased about 12–16 beats per minute. Other work has shown that this same effect occurs for aminophylline alone. Thus, there is no toxic effect reflected in pulse rate after bolus injection of dyphylline (20 mg/kg) into a horse whose plasma concentrations of theophylline are about 9–10 mcg/ml and the theophylline has had time to equilibrate. In both horses, there was some decrease in blood pressure when both drugs were given simultaneously. The decrease was not precipitous or dangerous. The total methylxanthine plasma concentration was about 120 mcg/ml (Horse 2).

It is surprising that these large total plasma concentrations of central stimulant methylxanthines did not produce visible signs of toxicity in the horses. Horses are known to be very sensitive to central nervous stimulants, which is a problem for the horse racing industry. For example, horses are about 20 times more sensitive than people to central nervous stimulation by procaine as reported by Tobin, T., et al. in "Pharmacology of Procaine in the Horse: Pharmacokinetics and Behavioral Effects", *Am. J. Vet. Res.* 38:637-647 (1977). Thus, the bolus injection of dyphylline in the presence of theophylline was not as toxic as expected.

EXAMPLE 4

One horse was administered acetyl promazine thiamyol sodium, quaifensin, and halothane to produce general anesthesia. Dyphylline (20 mg/kg) was given as an intravenous bolus injection in less than 15 seconds and aminophylline (10 mg/kg) was given as an infusion over about 20 minutes. Plasma and cerebral spinal fluid were collected and assayed by high pressure liquid chromatography for both dyphylline and theophylline. The data are shown in Table X.

TABLE X

Plasma and Cerebral Spinal Fluid Concentrations of Theophylline and Dyphylline in a Horse Receiving Intravenous Aminophylline (10 mg/kg) over 20 Minutes and Dyphylline (20 mg/kg) as a Bolus Injection

| | Plasma Concentration (mcg/ml) | | Cerebral Spinal Fluid Concentration (mcg/ml) | |
|---|---|---|---|---|
| Time | Theophylline | Dyphylline | Theophylline | Dyphylline |
| 0 | 0 | 0 | 0 | 0 |
| 30 mins | 10.3 | 24.1 | 5.1 | 3.6 |
| 1 hour | 6.2 | 13.8 | 5.3 | 4.2 |
| 2 hours | 7.7 | 13.6 | 5.3 | 5.2 |
| 3 hours | 6.1 | 8.6 | 5.3 | 7.3 |
| 4 hours | 5.7 | 7.0 | 5.3 | 6.2 |
| 24 hours | 3.3 | 2.0 | 2.0 | 2.0 |

The data (Table X) show that both theophylline and dyphylline penetrate into cerebral spinal fluid. Dyphylline is so polar and so rapidly cleared from the body compared to theophylline that the results are surprising. Generally, polar compounds like dyphylline are not nation half-life becomes about six hours, then the following Table XI can be constructed:

TABLE XI

Predicted average plasma concentrations in mcg/ml of theophylline and dyphylline when administered together.

| | Patient Weight in Pounds | | | | | |
|---|---|---|---|---|---|---|
| | 130 Pounds | | 156.8 pounds | | 250 pounds | |
| Theophylline Half-Life | Theophylline Plasma Concentrations | Dyphylline Plasma Concentrations | Theophylline Plasma Concentrations | Dyphylline Plasma Concentrations | Theophylline Plasma Concentrations | Dyphylline Plasma Concentrations |
| 3 hours | 4.8 | 40.0 | 4.0 | 33.2 | 2.5 | 20.8 |
| 7 hours | 11.1 | 40.0 | 9.3 | 33.2 | 5.8 | 20.8 |
| 10 hours | 15.8 | 40.0 | 13.1 | 33.2 | 8.3 | 20.8 | expected to cross the blood-brain barrier as readily as less polar compounds like theophylline. The data also show that the unexpectedly low toxicity for dyphylline in the presence of theophylline is not due to failure to penetrate into cerebral spinal fluid.

Rapid loading of drugs by "filling" the central compartment is a known procedure. However, the above methods of use of dyphylline are unique and unexpected since conventional wisdom dictates that this approach not be used for theophylline or related compounds, such as dyphylline, for the reasons listed earlier. Therefore, it is an aspect of this invention that derivatives can be rapidly intravenously administered without prior knowledge of whether or not a patient had been receiving theophylline-releasing compounds.

While the foregoing examples describe rapid intravenous administration of the derivative compounds, the data indicate that it should be safe to use other routes of rapid administration such as intramuscular injection and inhalation.

III. Dosage

Data in Example 1 and Example 2 can be used to simulate plasma concentrations of dyphylline and theophylline when administered together. This information is useful in determining an appropriate dosage of a product for the combined administration of theophylline and dyphylline, by sustained action or immediate release, to a wide range of subjects, e.g. of various body weights. In particular, the data can be used to select a dosage sufficient to provide a greater total plasma concentration of the methyl xanthine compounds than can safely be provided by either one of the compounds administered alone, e.g. a dosage wherein an amount of one of the compounds is added to a fully effective amount of the other.

The half-life of theophylline is known to vary widely among patients, usually varying from about three hours to about 9 hours if there is no serious hepatic disease. The total volume of distribution is somewhat less variable; as described by Winter in *Basic Clinical Pharmacokinetics*, Applied Therapeutics, Inc., p. 126, (1980). The average is about 0.48 L/kg. An equation which predicts the usual average plasma concentration at steady state for drugs obeying two compartment pharmacokinetics is $\bar{c} = FD/Vd\beta\Delta$ where $\bar{c}$ = average plasma concentration at steady state, F = fraction of the dose absorbed, Vd = total volume of distribution, $\beta$ = total body elimination rate constant, and $\Delta$ = dosing interval. If one assumes F=1.0, Vd=0.48 L/kg, $\Delta$=eight hours and dose administered is 250 mg for theophylline; and assumed F=1.0, Vd =0.8 L/kg, $\Delta$=eight hours, and the dose administered is 1.75 gm of dyphylline as a sustained action dosage form such that the slowed release affects the absorption rate such that the apparent elimination half-life becomes about six hours, then the following Table XI can be constructed:

Data in Table XI do not assume any effect of the two drugs on each other's volume of distribution. If there is an effect, then the observed plasma concentrations would be different than calculated, but the data in Example 1 indicates that toxicity should not develop from the combination administration. Similar tables could be developed for various doses of each drug and various apparent half-life values for dyphylline depending on the dosage form design. Of course, the "peak and valley" concentrations are greatly affected by the drug half-life.

Many dose combinations other than those shown in Table XI can be designed if lower total xanthine plasma concentrations are desired and effective as may very well be the case. Lower doses would be desirable since the total dose chosen for Table XI calculations is 2.0 gm which is much too large for a single tablet, especially with fillers and binders, etc. However, this example is not meant to be all inclusive, but shows that a single combination of dyphylline and theophylline could be administered to patients with markedly different pharmacokinetic characteristics and the total methylxanthine concentration would be in the effective concentration range but the combination would not be toxic. This is certainly not true for theophylline alone since a dose which is effective in a 250 pound person with a theophylline half-life of three hours would be expected to be very toxic, probably fatal, in a 130-pound person with a theophylline half-life of 10 hours.

EXAMPLE 5

To confirm the data shown in Table XI, dyphylline, 1000 mg, was administered to twelve healthy male volunteers as a zero-order infusion (50 mg/min) or as three conventional tablets (2×400 mg, 1×200 mg). Samples were analyzed as reported in Example 2. Semilogarythmic plots of typical dyphylline plasma concentration vs. time are shown in FIGS. 9A–11B (the y axes are plasma concentration in mcg/ml and the x axes are time in minutes). The avergage total volume of distribution for IV administration was 0.78 liters/kg with a standard deviation of 0.08. This demonstrates that the data shown in Table XI, which was based on only two subjects, is consistent for these two examples and valid for a much larger population, although different from the reports of Lawyer and Zuidema.

Maximum dyphylline plasma concentration after the 20-minute intravenous infusion averaged 30.1 mcg/ml and ranged from 18.4 mcg/ml to 46.8 mcg/ml. The cardiovascular effects are summarized in Table XII. The difference between predose and peak drug effects on diastolic and systolic blood pressure, as well as heart rate, were not statistically significant at the $\alpha = 0.05$ level. No subjects reported any drug related toxicities.

TABLE XII

| Subject Identification Number | Blood Pressure t(0)[a] (mmHg) | Blood Pressure T(cut)[b] (mmHg) | Heart Rate t(0) (beats/min) | Heart Rate T(cut) (beats/min) |
|---|---|---|---|---|
| 1 | 110/70 | 108/64 | 52 | 64 |
| 2 | 100/70 | 110/70 | 50 | 54 |
| 3 | 120/80 | 110/80 | 50 | 56 |
| 4 | 145/80 | 140/84 | 70 | 72 |
| 5 | 125/70 | 125/70 | 62 | 66 |
| 6 | 140/80 | 120/80 | 50 | 54 |
| 7 | 110/60 | 110/60 | 50 | 56 |
| 8 | 135/90 | 140/90 | 60 | 54 |
| 9 | 115/70 | 100/58 | 52 | 46 |
| 10 | 105/60 | 100/60 | 50 | 56 |
| 11 | 115/80 | 102/62 | 60 | 60 |
| 12 | 120/70 | 115/70 | 56 | 60 |
| Mean[e] | 120/73 | 115/71 | 55 | 58 |
| Range | 100–145/ 60–90 | 100–140/ 58–90 | 50–70 | 46–72 |

[a]Time zero.
[b]Time infusion stopped.

This example, when combined with earlier examples, shows that dyphylline can be dosed intravenously to clinically effective plasma concentrations without producing substantial toxicities. The rabbit data suggest this to be true even if the patient has been receiving theophylline.

IV. Combinations Including Various N-7-Substituted Derivatives of Theophylline Although the foregoing examples refer specifically to the administration of dyphylline, experiments indicate that it is also safe to administer certain other N-7-substituted derivatives of theophylline over a short period of time, i.e. less than two minutes. And, it also is found that such derivatives can be used with theophylline without potentiating toxicity. These derivatives include etophylline, proxyphylline, or a combination of such drugs or of one or both such drugs with dyphylline.

The dosage for each derivative would be adjusted to compensate for differences in potency. A loading dose, given over two minutes, could be used, and a zero-order infusion could additionally be used to maintain the desired plasma concentration of either drug. Due to rapid clearance of these drugs from the central compartment, it may be desirable to use a second loading "bolus" dose as described above in reference to dyphylline.

The amounts of theophylline and derivatives administered must be sufficient, in combination, to achieve a therapeutic effect. But, it is not necessary that any compound be present in an amount independently sufficient to have a therapeutic effect. Best results are achieved if one or both of the theophylline and derivatives are present in an independently effective amount, so long as the amount of theophylline does not exceed the toxic level (20 mcg/ml for humans).

The amounts administered should be sufficient to provide a minimum total plasma concentration of methyl xanthine that is greater than 10 mcg/ml. Most advantageously, the concentration can be greater than 20 mcg/ml. To achieve such concentrations, any one of the derivatives can be administered to provide a derivative plasma concentration of at least 10 mcg/ml in a subject who also receives a nontoxic dose of theophylline. Dyphylline can be administered at about 8 to 35 mg/kg of body weight by I.V bolus to produce a plasma concentration, after equilibrium, of at least about 10 mcg/ml, which can be followed by zero order infusion at a rate of about 2.5 to 12 mg/kg of body weight per hour to maintain an effective amount in the body. Etophylline can be administered at about 5.5 to 25 mg/kg of body weight by I.V. bolus, optionally followed by zero order infusion at about 1.5 to 5 mg/kg of body weight per hour. Proxyphylline can be admixed at about 5.5 to 25 mg/kg of body weight by I.V. bolus, optionally followed by zero order infusion at about 0.75 to 2.5 mg/kg of body weight per hour.

Use of the various derivatives is described in the following Example 6.

EXAMPLE 6

The drugs dyphylline, proxyphylline, etophylline, and theophylline were administered intravenously to female rabbits according to the scheme shown below in Table XIII.

TABLE XIII

| Group I | T | T/D | T/E | T/P |
|---|---|---|---|---|
| Group II | D | D/T | D/E | D/P |
| Group III | E | E/T | E/D | E/P |
| Group IV | P | P/T | P/D | P/E |

T - 40 mg/kg of aminophylline infused at the rate of 0.21 ml/min over 30 mins.
T/D - 40 mg/kg of aminophylline infused at the rate of 0.21 ml/min over 30 min. Wait 30 min. 300 mg/kg of dyphylline as loading dose at the rate of 1.02 ml/min. 100 mg/kg/hr of dyphylline as maintenance dose at the rate of 0.08 ml/min for 2 hrs.
T/E - 40 mg/kg of aminophylline infused at the rate of 0.21 ml/min over 30 min. Wait 30 min. 150 mg/kg of etophylline as loading dose at the rate of 1.02 ml/min. 35 mg/kg/hr of etophylline as maintenance dose at the rate of 0.08 ml/min for 2 hrs.
T/P - 40 mg/kg of aminophylline infused at the rate of 0.21 ml/min over 30 min. Wait 30 min. 135 mg/kg of proxyphylline as loading dose at the rate of 1.02 ml/min. 15 mg/kg/hr of proxyphylline as maintenance dose at the rate of 0.08 ml/min for 2 hrs.
D - 300 mg/kg of dyphylline infused at the rate of 1.02 ml/min.
D/T - 300 mg/kg of dyphylline infused at the rate of 1.02 ml/min. Wait 30 mins. 40 mg/kg of aminophylline infused at the rate of 0.21 ml/min over 30 mins.
D/E - 300 mg/kg of dyphylline infused at the rate of 1.02 ml/min. Wait 30 min. 150 mg/kg of etophylline as loading dose at the rate of 1.02 ml/min. 35 mg/kg/hr of etophylline as maintenance dose infused at the rate of 0.08 ml/min over 2 hrs.
D/P - 300 mg/kg of dyphylline infused at the rate of 1.02 ml/min. Wait 30 min. 135 mg/kg of proxyphylline as loading dose infused at the rate of 1.02 ml/min. 15 mg/kg/hr of proxyphylline as maintenance dose infused at the rate of 0.08 ml/min over 2 hrs.
E - 150 mg/kg of etophylline infused at the rate of 1.02 ml/min.
E/T - 150 mg/kg of etophylline infused at the rate of 1.02 ml/min. Wait 30 mins. 40 mg/kg of aminophylline infused at the rate of 0.21 ml/min over 30 mins.
E/D - 150 mg/kg of etophylline infused at the rate of 1.02 ml/min. Wait 30 min. 300 mg/kg of dyphylline as loading dose infused at the rate of 1.02 ml/min. 100 mg/kg/hr of dyphylline as maintenance dose infused at the rate of 0.08 ml/min over 2 hrs.
E/P - 150 mg/kg of etophylline infused at the rate of 1.02 ml/min. Wait 30 min. 135 mg/kg of proxyphylline as loading dose infused at the rate of 1.02 ml/min. 15 mg/kg/hr of proxyphylline as maintenance dose infused at the rate of 0.08 ml/min over 2 hrs.
P - 135 mg/kg of proxyphylline infused at the rate of 1.02 ml/min.
P/T - 135 mg/kg of proxyphylline infused at the rate of 1.02 ml/min. Wait 30 mins. 40 mg/kg of aminophylline infused at the rate of 0.21 ml/min over 30 mins.
P/D - 135 mg/kg of proxyphylline infused at the rate of 1.02 ml/min. Wait 30 min. 300 mg/kg of dyphylline as loading dose infused at the rate of 1.02 ml/min. 100 mg/kg/hr of dyphylline as maintenance dose infused at the rate of 0.08 ml/min over 2 hrs.
P/E - 135 mg/kg of proxyphylline infused at the rate of 1.02 ml/min. Wait 30 min. 150 mg/kg of etophylline as loading dose infused at the rate of 1.02 ml/min. 35 mg/kg/hr of etophylline as maintenance dose infused at the rate of 0.08 ml/min over 2 hrs.

Note: All drugs were prepared in a dextrose 5% in water solution to adjust the solutions so they did not hemolyse red blood cells.

Only six rabbits died during the experiments and none of the deaths appeared to be from any of the drug treatments administered as shown in Table XIII. These results are quite surprising since the theophylline dose alone was close to lethal (see Example 1). Combined methyl xanthine plasma concentrations were often in the 700 mcg/ml to over 1000 mcg/ml range. In some cases, the drugs seemed to interact to displace each other from their binding sites and produce higher than expected plasma concentrations of one or both methylxanthines with perturbed drug concentrations vs. time curves, but the effects were not toxic to the degree expected.

In some cases, individual drug treatments produced substantial slowing of heart rate, e.g. for one rabbit with proxyphylline the heart rate decreased to about 96 beats per minute (bpm); for dyphylline one decreased to 76 bpm; and for etophylline the decrease for one was to 100 bpm. Normal is about 220 bpm. Most unexpectedly, the heart rate returned to near normal or normal, even when a second methyl xanthine was administered to the animal. After adding dyphylline on top of proxyphylline (for single example listed above), the heart rate returned to normal. After adding etophylline on top of dyphylline (for single example listed above), the heart rate returned to 180 bpm. After adding proxyphylline to etophylline (single example above), the heart rate returned to 250 bpm. The finding that the combination of drugs did not depress pulse rate substantially is most unexpected, especially with the large doses given.

Two rabbits died from convulsions when doses even more concentrated than those shown in Table XIII were inadvertently administered. A third rabbit died more than 12 hours after treatment was stopped. Three other deaths occurred 3 hours, 5 hours, and 8 hours after drug administration was stopped. No one treatment was involved, as the treatments were E/P, P/D, an T/E respectively. The time periods for death are well after drug distribution equilibration in tissues is reached and may be due to the drugs, since methyl xanthines are toxic. On the other hand, these rabbits, as "sensitive" members of the population, may have died due to some treatment effect other than the drugs. The rate of drug administration was limited by the volume of fluid which could be administered to the rabbits without producing fluid build-up in the lungs. None of the last four deaths was preceded by convulsions. Each rabbit just quietly died, which is not typical if death is induced by methyl xanthines. The remarkable finding with the very large doses of methyl xanthines being given rapidly and intravenously is that toxicities were far less than one would expect.

While I have described and given examples of several embodiments of my invention, it will be apparent to those skilled in the art that changes and modifications may be made without departing from my invention in its broader aspects. Therefore, the scope of the invention is only defined by the appended claims.

I claim:

1. A method of treating bronchopulminary insufficiency of a human or other warm blooded animal subject, without toxic side effects, the method comprising:
   administering the drug theophylline a theophylline-releasing drug to the subject in an amount insufficient to produce a plasma concentration thereof at which the subject would experience a toxic effect if theophylline were administered alone; and
   administering an N-7 substituted derivative of theophylline selected from the group consisting of dyphylline, etophylline, proxyphylline, and mixtures thereof to the subject in an amount insufficient to produce a plasma concentration thereof at which the subject would experience a toxic effect if the derivative was administered alone;
   the amounts administered being such that the total plasma concentration of dimethyl xanthine is greater than the concentration at which the subject would experience a toxic effect if the total plasma concentration were provided by theophylline alone.

2. The method of claim 1 wherein the derivative and a source of the theophylline are provided intravenously in the same dosage form.

3. The method of claim 1 wherein the theophylline is provided in the body of a subject, by administering to the subject, a theophylline-releasing drug.

4. The method of claim 3 wherein the theophylline-releasing drug is aminophylline.

5. The method of claim 1 wherein each of the derivative and the theophylline is present in the body in an amount independently sufficient to have a therapeutic effect.

6. The method of claim 1 wherein the theophylline is present in the body in an amount sufficient to have a therapeutic effect.

7. The method of claim 1 wherein the derivative is present in the body in an amount independently sufficient to have a therapeutic effect and theophylline is present in an amount that is not independently sufficient to have a therapeutic effect.

8. The method of claim 1 wherein the total plasma concentration is greater than 20 mcg/ml.

9. A method of treating bronchopulminary insufficiency of a human or other warm blooded animal subject, without toxic side effects, the method comprising administering, intravenously, intramuscularly, or in the lungs, an N-7-substituted derivative of theophylline selected from the group consisting of dyphylline, etophylline, proxyphylline and mixtures thereof, to a subject which has been taking the drug theophylline or a theophylline-releasing drug, the derivative being given in an amount sufficient that the subject's total plasma concentration of dimethyl xanthine is greater than 20 mcg/ml and insufficient to produce a plasma concentration of the derivative at which the subject would experience a toxic effect if the derivative was administered alone.

10. The method of claim 9 wherein the derivative is administered intravenously.

11. The method of claim 9 wherein the derivative is administered intramuscularly.

12. The method of claim 9 wherein the derivative is administered in the lungs.

* * * * *

UNITED STATES PATENT AND TRADEMARK OFFICE
CERTIFICATE OF CORRECTION

PATENT NO. : 4,581,359
DATED : April 8, 1986
INVENTOR(S) : JAMES W. AYRES

It is certified that error appears in the above-identified patent and that said Letters Patent is hereby corrected as shown below:

In the References Cited:

Page 2, col. 1, "i" should be deleted and "Toxicol." should be in italics in the Merkus et al. reference.

In the Specification:

Col. 4, line 41, "Propyphylline" should be --Proxyphylline--.

Col. 13, line 53, "ug" (greek mu) should be --mg--.

In the Claims:

Claim 1, line 4, insert --or-- after "theophylline".

Claim 1, line 9 (top of Column 28), insert a hyphen between "7" and "substituted".

Signed and Sealed this

Fourteenth Day of October, 1986

[SEAL]

Attest:

DONALD J. QUIGG

Attesting Officer     Commissioner of Patents and Trademarks